US009488573B2

(12) United States Patent
Edwards et al.

(10) Patent No.: US 9,488,573 B2
(45) Date of Patent: Nov. 8, 2016

(54) ACOUSTO-ELECTROMAGNETIC INVESTIGATION OF PHYSICAL PROPERTIES OF AN OBJECT

(71) Applicant: ISIS INNOVATION LIMITED, Oxford, Oxfordshire (GB)

(72) Inventors: David John Edwards, Oxford (GB); Pithawat Vachirimon, Oxford (GB)

(73) Assignee: ISIS INNOVATION LIMITED, Oxford, Oxfordshire (GB)

( * ) Notice: Subject to any disclaimer, the term of this patent is extended or adjusted under 35 U.S.C. 154(b) by 368 days.

(21) Appl. No.: 14/346,462

(22) PCT Filed: Sep. 19, 2012

(86) PCT No.: PCT/GB2012/052310
§ 371 (c)(1),
(2) Date: Mar. 21, 2014

(87) PCT Pub. No.: WO2013/041856
PCT Pub. Date: Mar. 28, 2013

(65) Prior Publication Data
US 2014/0224021 A1 Aug. 14, 2014

(30) Foreign Application Priority Data

Sep. 23, 2011 (GB) .................................. 1116518.0

(51) Int. Cl.
*G01N 21/47* (2006.01)
*G01N 29/06* (2006.01)
(Continued)

(52) U.S. Cl.
CPC ............. *G01N 21/47* (2013.01); *A61B 5/0048* (2013.01); *A61B 5/0059* (2013.01); *A61B 5/05* (2013.01);
(Continued)

(58) Field of Classification Search
CPC A61B 5/0048; A61B 5/7228; A61B 5/0507; A61B 5/0059; A61B 5/05; A61B 5/0051; G01N 21/1717; G01N 21/47; G01N 29/0654; G01N 21/1702; G01N 21/3581; G01N 2291/017; G01S 13/89; G01S 13/50; G01S 13/862; G01S 15/899
USPC .......................................... 73/601
See application file for complete search history.

(56) References Cited

U.S. PATENT DOCUMENTS 5,099,848 A 3/1992 Parker et al.
5,174,298 A 12/1992 Dolfi et al.
(Continued)

FOREIGN PATENT DOCUMENTS

EP 0832599 A1 4/1998
EP 1039313 A1 9/2000
(Continued)

OTHER PUBLICATIONS

Braunreiter et al., "On the Use of Space-Time Adaptive Processing and Time-Frequency Data Representation for Detection of Near-Stationary Targets in Monostatic Clutter" Proc. 10th IEEE Workshop on Statistical Signal and Array Processing. pp. 472-475. (2000).

(Continued)

*Primary Examiner* — J M Saint Surin
(74) *Attorney, Agent, or Firm* — Harness, Dickey & Pierce, P.L.C.

(57) ABSTRACT

An imaging system for an object such as human or animal tissue applies acoustic vibrations localized in two or three dimensions and simultaneously illuminates the object with an illuminating electromagnetic wave. The acoustic vibration comprises a carrier wave that is amplitude modulated by an AM waveform. The carrier wave is selected to provide the localization of the acoustic vibration, whereas the AM waveform includes a frequency component selected to provide a vibration of the object of greater magnitude than the carrier wave. To detect a Doppler component shifted by the frequency of said frequency component of the AM waveform, a signal processing apparatus comprises a phase locked-loop locked to the EM frequency, producing a frequency-demodulated signal comprising the set of the Doppler components, and a lock-in amplifier configured to extract a signal at a reference frequency equal to the frequency of a frequency component of the AM waveform.

36 Claims, 9 Drawing Sheets

(51) Int. Cl.
  *A61B 5/00* (2006.01)
  *A61B 5/05* (2006.01)
  *G01S 13/89* (2006.01)
  *G01S 13/50* (2006.01)
  *G01S 13/86* (2006.01)
  *G01N 21/17* (2006.01)
  *G01S 15/89* (2006.01)
  *G01N 21/3581* (2014.01)

(52) U.S. Cl.
  CPC .......... *A61B 5/0507* (2013.01); *A61B 5/7228* (2013.01); *G01N 21/1717* (2013.01); *G01N 29/0654* (2013.01); *G01S 13/50* (2013.01); *G01S 13/862* (2013.01); *G01S 13/89* (2013.01); *A61B 5/0051* (2013.01); *G01N 21/1702* (2013.01); *G01N 21/3581* (2013.01); *G01N 2291/017* (2013.01); *G01S 15/899* (2013.01)

(56) References Cited

U.S. PATENT DOCUMENTS

| | | | |
|---|---|---|---|
| 5,212,667 | A | 5/1993 | Tomlinson, Jr. et al. |
| 5,293,873 | A | 3/1994 | Fang |
| 6,002,958 | A | 12/1999 | Godik |
| 6,245,015 | B1 | 6/2001 | Pattanayak |
| 6,645,144 | B1 | 11/2003 | Wen et al. |
| 6,738,653 | B1 | 5/2004 | Sfez et al. |
| 6,957,099 | B1 | 10/2005 | Arnone et al. |
| 6,974,415 | B2 | 12/2005 | Cerwin et al. |
| 1,237,956 | A1 | 9/2011 | Edwards et al. |
| 8,400,166 | B2 * | 3/2013 | Geren ............... G01R 27/00 324/637 |
| 9,164,033 | B2 * | 10/2015 | Edwards ............ A61B 5/0048 |
| 2005/0100866 | A1 | 5/2005 | Arnone et al. |
| 2005/0256403 | A1 | 11/2005 | Fomitchov |
| 2006/0122475 | A1 | 6/2006 | Balberg et al. |
| 2007/0015992 | A1 | 1/2007 | Filkins et al. |
| 2007/0038095 | A1 | 2/2007 | Greenleaf et al. |
| 2007/0187632 | A1 | 8/2007 | Igarashi |
| 2007/0233056 | A1 | 10/2007 | Yun |
| 2008/0161674 | A1 | 7/2008 | Monro |
| 2008/0179526 | A1 * | 7/2008 | Xu ..................... G01J 3/10 250/339.07 |
| 2009/0069687 | A1 | 3/2009 | Igarashi |
| 2009/0264722 | A1 | 10/2009 | Metzger et al. |
| 2009/0281422 | A1 | 11/2009 | Salama et al. |
| 2009/0316854 | A1 | 12/2009 | Ismail et al. |
| 2010/0036240 | A1 | 2/2010 | Ismail et al. |
| 2010/0328142 | A1 * | 12/2010 | Zoughi ............... G01S 7/025 342/179 |
| 2012/0262190 | A1 * | 10/2012 | Kondo ............... G01N 21/3581 324/639 |
| 2015/0265158 | A1 * | 9/2015 | Edwards ............. G01N 22/00 600/407 |

FOREIGN PATENT DOCUMENTS

| | | | | |
|---|---|---|---|---|
| EP | 1675501 | A2 | 7/2006 | |
| EP | 1810610 | A1 | 8/2007 | |
| EP | 2016891 | A1 | 1/2009 | |
| EP | 2378272 | A1 | 10/2011 | |
| GB | 1326612 | A | 8/1973 | |
| GB | 201116518 | * | 11/2011 | .......... A61B 5/0048 |
| JP | 63246627 | A | 10/1988 | |
| JP | 2000298776 | A | 10/2000 | |
| WO | WO-95/33987 | A1 | 12/1995 | |
| WO | WO-98/54600 | A1 | 12/1998 | |
| WO | WO-01/65240 | A1 | 9/2001 | |
| WO | WO-02/08740 | A2 | 1/2002 | |
| WO | WO-2006097910 | A1 | 9/2006 | |
| WO | WO-2008040771 | A2 | 4/2008 | |
| WO | WO-2010043851 | A1 | 4/2010 | |

OTHER PUBLICATIONS

Buerkle & Sarabandi "Analysis of Acousto-Electromagnetic Scattering from a Dielectric Cylinder Using the Finite-Difference Time-Domain Method" Proceeding: IEEE Interaction Antennas and Propagation & URSI Symposium, Alburquerque, NM, pp. 3279-3281. Jul. 9-14, 2006.
Chen & Lipps "Time-Frequency Signatures of Micro-Doppler Phenomenon for Feature Extraction" Proc os SPIE Conference on Wavelet Applications VII, vol. 4056, Orlando, FL. USA pp. 220-226 (2000).
Chen, "Analysis of Rada Micro-Doppler Signature With Time-Frequency Transform" Proceedings of the 10th IEEE Workshop on Statistical Signal and Array Processing. pp. 463-466. (2000).
Greneker "Extraction of Micro-Doppler from Vehicle Targets at X-Band Frequencies" Proc of SPIE Conference on Radar Sensor Technology VI, vol. 4371, pp. 1-9. (2001).
Géza Kolumbán: "Phase-Locked Loops" In: The Encyclopedia of RF and Microwave Engineering, vol. 4, Jan. 1, 2005.
Ian Poole: "PLL FM demodulator/detector", Adrio Communications Ltd, Jun. 13, 2011.
Lawrence and Sarabandi "Electromagnetic Scattering from Vibrating Metallic Objects Using Time-Varying Generalized Impedance Boundary Conditions" IEEE Transactions on Antennas and Propagation, vol. 2. pp. 782-785. Jan. 2002.
Richmond "A Modulated Scattering Technique for Measurement of Field Distributions" IRE Trans. Microwave Theory and Techniques. vol. 3, pp. 13-15. (1955).
Schmitt & Sengupta, "On the Reflection of Electromagnetic Waves from a Medium Excited by Acoustic Waves" Journal of Applied Physics, vol. 31, No. 2. pp. 439-440. (1960).
Schnitt & Wu "Electromagnetic Reflection from Sound Waves" J. Acoust. Soc. Am., vol. 32, Issue 12, pp. 1660-1667 (1960).
Lawrence et al., "Electromagnetic Scattering from Vibrating Penetrable Objects Using a General Class of Time-Varying Sheet Boundary Conditions", IEEE Transactions on Antennas and Propagation, vol. 54, No. 7, pp. 2054-2061, Jul. 2006.

* cited by examiner

ACOUSTO-ELECTROMAGNETIC INVESTIGATION OF PHYSICAL PROPERTIES OF AN OBJECT

CROSS-REFERENCE TO RELATED APPLICATIONS

This application is a 371 U.S. National Stage of International Application No. PCT/GB2012/052310, filed Sep. 19, 2012, which claims priority to British Patent Application No. GB 1116518.0, filed Sep. 23, 2011. The disclosures of the above applications are incorporated herein by reference.

The present invention relates to the investigation of physical properties of an object. It has application in the field of imaging although not exclusively.

Various methods for investigating the physical properties of an object are known. For example there are a wide range of imaging techniques which produce an image of an object representing its physical properties. For example in the field of medical imaging, established and widely used imaging methods include x-ray radiography, computed tomography (CT), ultrasound imaging, magnetic resonance imaging (MRI), positron emission tomography (PET).

Different imaging methods are based on different physical phenomena. For example in x-ray radiography and computed tomography (CT) x-rays interact with the object, in ultrasound imaging ultrasound interacts with the object, and so on. As a result different imaging techniques produce images of different physical characteristics of the object being imaged and different imaging techniques have different advantages and limitations.

The choice of modality depends on the properties of the tissue being interrogated, for example x-rays may be suitable for high hard and calcified tissues, MRI for soft tissues and ultrasound for imaging changes in mechanical properties.

By way of example, comparing both of the common medical imaging methods of ultrasound imaging and MRI provide relatively high resolution images, but ultrasound imaging provides images of acoustic or mechanical properties whereas MRI provides images of electromagnetic properties. Thus MRI provides a useful contrast mechanism that is particularly useful in the medical imaging field because it shows essentially dielectric differences present in many tissue types. Conversely MRI suffers from the problems of being relatively expensive and of requiring powerful magnets.

Also, there are a range of spectroscopic techniques based on different physical phenomena. Such spectroscopic techniques do not necessarily produce an image but provide data in respect of a range of frequencies or wavelengths, for example of electromagnetic radiation.

In the medical sphere there is a growing field of imaging systems based on dielectric contrast that provide additional information for clinicians in determining tissue types, typically in conjunction with ultrasound and x-rays. One proposed method is microwave imaging, which has been under active research since 1998.

Ultra wideband radar systems have also been investigated to provide balance between attenuation and resolution. This type of approach has been changed to produce good quality images, but only recently have there been developed image reconstruction algorithms which approach the potential resolution of this approach.

Due to the different physical phenomena on which they are based, such different imaging techniques and different spectroscopic techniques have different applications, depending on the nature of the features of interest in the object.

WO-2010/043851 discloses a further type of imaging that may be referred to as being acousto-electromagnetic in that it involves applying acoustic vibration to an object simultaneously with illuminating the object with an illuminating electromagnetic wave.

The vibration of the object scatters and modulates the illuminating electromagnetic wave, generating a scattered electromagnetic wave including Doppler components shifted from the frequency of the illuminating electromagnetic wave by frequencies of the vibration of the object under the acoustic vibration and multiples thereof. The received scattered wave is received and data representing characteristics of the Doppler components such as amplitude and phase is derived. The detected characteristics are dependent on the mechanical response of the object and on the electromagnetic properties of the object, which cause an interaction with the illuminating electromagnetic wave. Thus the detected characteristics provide information on electromagnetic properties similar to MRI imaging but without requiring magnets.

However, the method disclosed in WO-2010/043851 makes use of acoustic vibration that is localized in a region of the object, for example using similar techniques to known ultrasound imaging. This means that the method provides information from just that region, because that is where the scattered Doppler components are generated. As a result, the resolution of the imaging is similar to that achieved by ultrasound imaging, being limited by the localization achievable on the basis of the wavelength of the acoustic vibration.

This combination of providing information on electromagnetic properties, with a resolution derived from acoustic vibration offers advantages that may provide effective imaging in a range of fields.

The first aspect of the present invention is concerned with the selection of the acoustic vibration.

This selection needs to take into account the following characteristics of the imaging. A first factor is that the choice of frequency impacts on the resolution of the imaging that may be achieved. This is because the method involves localisation of the acoustic vibration in a region of the object from which the scattered Doppler components are generated. The second factor is that the magnitude of the acoustic vibration of the object is also dependent on the frequency of the acoustic vibration. This effect derives simply from the mechanical properties of the object under investigation. For some objects, these two factors can compete, requiring careful choice of the frequency of the acoustic vibration in order to balance these factors.

The first aspect of the present invention is concerned with optimising the selection of the acoustic vibration.

According to a first aspect of the present invention, there is provided a method of investigating physical properties of an object, comprising:

applying to the object acoustic vibration localised in two or three dimensions in a region in the object, the acoustic vibration comprising a carrier wave that is amplitude modulated by an AM waveform, the carrier wave being selected to provide the localization of the acoustic vibration and the AM waveform including a frequency component selected to provide a vibration of the object of greater magnitude than the carrier wave;

simultaneously illuminating the object with an illuminating electromagnetic wave that has an EM frequency in a range extending up to 30 THz, the vibration direction of the acoustic vibration having a component parallel to the propagation direction of the illuminating electromagnetic wave so that the acoustic vibration of the object in the region generates a scattered electromagnetic wave including a set of Doppler components shifted from the frequency of the illuminating electromagnetic wave by frequencies of the vibration of the object caused by the acoustic vibration and multiples thereof; and receiving the scattered electromagnetic wave generated in the region, detecting, from the received, scattered electromagnetic wave, a Doppler component shifted from the frequency of the illuminating electromagnetic wave by the frequency of said frequency component of the AM waveform; and outputting a signal representing at least one characteristic of the detected Doppler component.

Further according to the first aspect of the present invention, there is provided a system capable of implementing a similar method.

The present invention provides a method of investigating the physical properties of an object using a similar acousto-electromagnetic technique to that described WO-2010/043851 that involves applying acoustic vibration to an object localised in two or three dimensions in a region in the object simultaneously with illuminating the object with an illuminating electromagnetic wave. However, the present invention utilizes a specific form of acoustic vibration that comprises a carrier wave that is modulated by an AM waveform. This acoustic vibration is optimised to provide advantages during imaging. In particular, the carrier wave is selected to provide the localisation of the acoustic vibration, whereas the AM waveform is chosen to include a frequency component that provides a vibration of the object. The nature of amplitude modulation is that the carrier wave has a higher frequency than the AM waveform. Thus, the AM waveform may be selected to provide a vibration of the object of greater magnitude than the carrier wave. Thus the present invention proves the flexibility in the choice of the selection of the acoustic waveform, particularly for objects where the desired resolution requires the use of a frequency that provides a low mechanical response. Such subjects, the carrier wave may be selected to optimize the resolution and the AM waveform may be independently chosen to provide a significant mechanical response.

The AM waveform may take a variety of forms. In its simplest form, the AM waveform may be a single frequency component, that is a sinusoidal waveform at a given frequency. However, other waveforms having a fundamental frequency component and harmonic frequency components may also be used, and can in some instances have the benefit of being easy to generate. For example, the AM waveform may be a square wave, which is particularly easy to generate simply by pulsing the carrier waveform on and off.

Where the AM waveform has multiple frequency components, then in principle to detect Doppler components shifted from the frequency of the illuminating electromagnetic wave i.e. frequency of any of the frequency components of the AM waveform. However, desirably there is used the fundamental frequency component the AM waveform, because this will generally provide the frequency component of the largest magnitude and will provide the maximum response. Furthermore, the fundamental frequency component is most easily isolated because it has relatively large separation from other Doppler components.

The frequency component of the AM waveform that is utilized is selected having regard to the relevant mechanical properties of the object. To optimize the response, this frequency component desirably has a period of the same order of magnitude as the acoustic relaxation time of the object in the regions under investigation.

The second aspect of the present invention is concerned with improving the sensitivity of detection of the Doppler components in a scattered electromagnetic wave in a method using an acousto-electromagnetic technique. This is desirable because the Doppler components are small in magnitude compared to the illuminating electromagnetic wave. Due to the localisation of the acoustic vibration, the scattered electromagnetic wave is generated only in the region in the object under investigation, so the source of the Doppler components has a small volume. The small magnitude of the Doppler components means that they will be subject to noise that is inherent in the system, and so will have a low signal-to-noise ratio (SNR).

According to a second aspect of the present invention, there is provided a method of investigating physical properties of an object, comprising:

applying to the object acoustic vibration localised in two or three dimensions in a region in the object;

simultaneously illuminating the object with an illuminating electromagnetic wave that has an EM frequency in a range extending up to 30 THz, the vibration direction of the acoustic vibration having a component parallel to the propagation direction of the illuminating electromagnetic wave so that the acoustic vibration of the object in the region generates a scattered electromagnetic wave including a set of Doppler components shifted from the frequency of the illuminating electromagnetic wave by frequencies of the vibration of the object caused by the acoustic vibration and multiples thereof; and receiving the scattered electromagnetic wave generated in the region, supplying the received, scattered electromagnetic wave to a phase-locked loop locked to the EM frequency to produce a frequency-demodulated signal comprising the set of the Doppler components frequency-demodulated from EM frequency;

supplying the frequency-demodulated signal to a lock-in amplifier configured to extract a signal at a reference frequency equal to a frequency of a frequency component of the vibration caused by the acoustic vibration; and outputting a signal representing at least one characteristic of the extracted signal.

Further according to the second aspect of the present invention, there is provided a system capable of implementing a similar method.

The detection of the Doppler component essentially requires frequency demodulation of those Doppler components from the components of the scattered electromagnetic wave of the same frequency as the illuminating electromagnetic wave. The second aspect of the present invention involves use of a phase-locked loop (PLL) in combination with a lock-in amplifier. The phase-locked loop is locked to the EM frequency and therefore produces a frequency-demodulated signal comprising all the set of Doppler components frequency-demodulated from the EM frequency. This frequency-demodulated signal is supplied to a lock-in amplifier, which is configured to extract a signal at a reference frequency equal to the frequency of the vibration of the object. If the acoustic vibration contains a single frequency component, then the reference frequency will be the frequency of that frequency component. Conversely, if the acoustic vibration comprises a carrier wave amplitude modulated by an AM waveform, in accordance with the first aspect of the present invention, then the reference frequency may be the frequency of the frequency component of the AM modulation that is being utilised. Thus, it is clear that the first and second aspects of the present invention may be combined. Accordingly, any of the features of the first and second aspects of the present invention may be combined together in any combination.

This combination of a phase-locked loop and a lock-in amplifier permits the detection of Doppler components of an extremely low level. For example, in frequency modulation terms, the embodiments described hereinafter have been arranged to detect modulation indexes of the order of ten parts in a million or better. This allows the acousto-electromagnetic method to be applied to investigate the properties of an object with a high degree of sensitivity, allowing accurate discrimination between different properties of the object.

The following comments apply equally to the first and second aspects of the present invention.

The present invention may be applied to provide imaging of the object. In this case the acoustic vibration is applied simultaneously or sequentially in a localised manner in a plurality of regions with different amplitude modulation applied to the ultrasound excitation in each region and the scattered electromagnetic wave generated in each of the plurality of regions is received and used to derive data representing the at least one characteristic of the detected Doppler component in respect of each region as image data. In this way, it is possible to generate image data for a plurality of regions and thus build up an image representing information on the physical properties of the object. In the case that the acoustic vibration is localised in two dimensions, then the regions extend in the third direction and thus the image is a two dimensional image (or shadow image). In the case that the acoustic vibration is localised in three dimensions, then the regions are limited in extent in that third direction and a three-dimensional image may be derived.

The acoustic vibration may be applied localised at the plurality of regions sequentially. In this case, the acoustic vibration may have the same frequency which simplifies implementation of the method but is not essential.

Alternatively, the acoustic vibration may be applied localised in the plurality of regions simultaneously but utilizing different frequency components in each region. In this case, frequency components applied to each region have different frequencies with the result that the electromagnetic waves scattered from each region have different frequencies, allowing the Doppler components simultaneously generated in respect of each region to be separated and used to derive the image data representing at least one characteristic of the Doppler components in respect of each region.

In principle, the present invention may also be used applying the acoustic vibration to just a single region without providing imaging of the object. In this case, the information on the physical properties of the object which is derived is useful nonetheless because it is based on the physical phenomenon described above.

These properties mean that the imaging of the present invention can provide advantages over the established imaging methods when applied to imaging human or animal tissue, including but not limited to medical imaging.

To allow better understanding, embodiments of the present invention will now be described by way of non-limitative example with reference to the accompanying drawings, in which.

Figure 1:
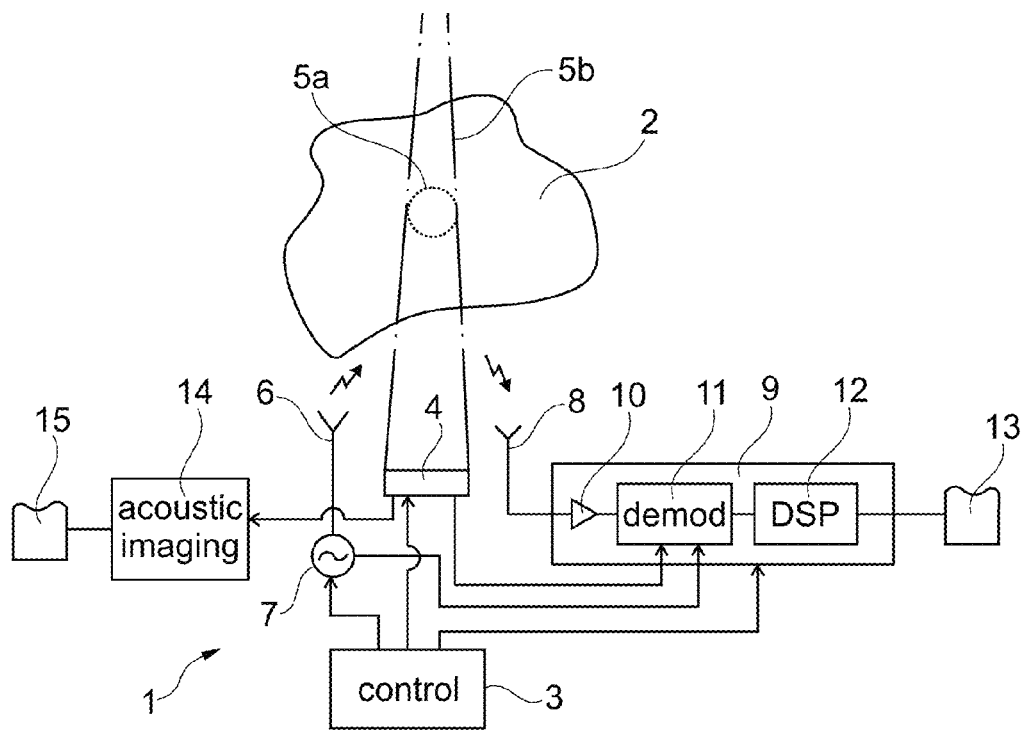
FIG. 1 is a diagram of an imaging system.

There will first be described a system 1 for investigating physical properties of an object 2, as shown in FIG. 1. The object 2 may be a biological object, for example human or animal tissue, in which case the system 1 may be applied in the field of medical imaging. However, the present invention is not restricted to that field and may be applied to a range of objects in other technical fields.

The system 1 includes a control unit 3 which controls the other components of the system 1. The control unit 3 may be implemented by a computer apparatus running an appropriate program.

The system 1 includes an acoustic transducer apparatus 4 which operates under the control of the control unit 3. The acoustic transducer apparatus 4 in operation applies acoustic vibration to the object 2.

The nature of the acoustic vibration is as follows. The acoustic vibration comprises a carrier wave amplitude modulated by an AM waveform that is periodic.

Figure 2:
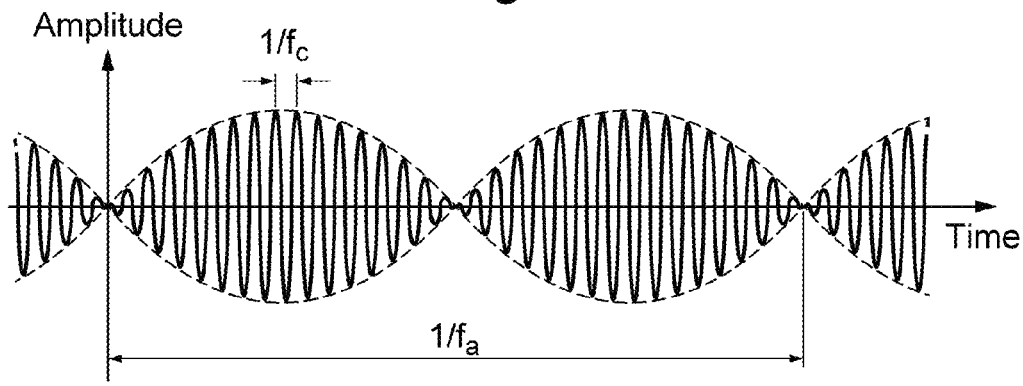
FIGS. 2 and 3 are graphs of two alternative waveforms of the acoustic vibration.
Figure 3:
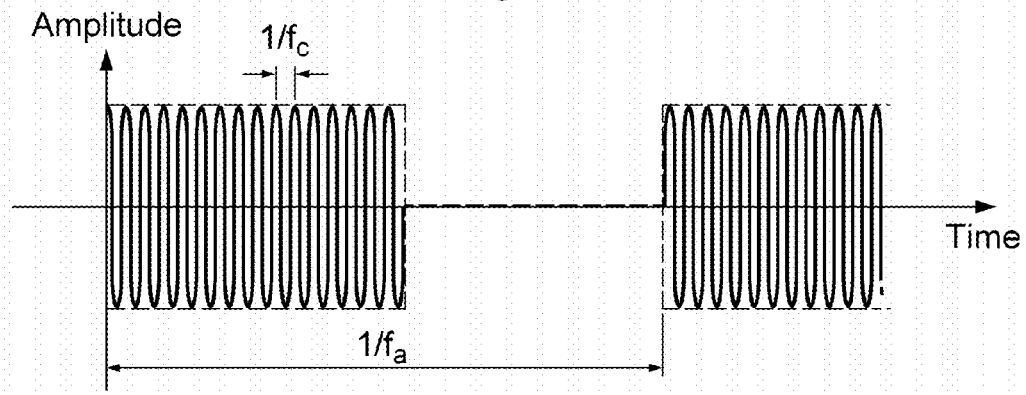

Two non-limitative examples of suitable acoustic waveforms are shown in FIGS. 2 and 3, wherein the carrier wave has in both cases a frequency fc. In FIG. 2, the AM waveform has its simplest form comprising a fundamental frequency component of frequency fa. In FIG. 3, the AM waveform is a square wave having a period of (1/fa), and hence comprising a fundamental frequency component of frequency fa and harmonic frequency components that are multiples of frequency fa.

The carrier wave is most simple to generate if it is a simple sinusoidal wave as shown in FIGS. 2 and 3, although in general, the carrier wave could have any other suitable waveform.

In general, the AM waveform may have a wide range of forms, but the use of the square wave as in the example of FIG. 3 is advantageous in that it is very easily generated by pulsing the carrier wave on and off. In the example of FIG. 3, the AM waveform is a square wave having equal on and off periods but this is not essential and it could be a square wave having unequal on and off periods. The nature of amplitude modulation is that carrier wave has a frequency that is smaller than the frequency of at least the fundamental frequency component of the AM waveform, and typically of one or more of the harmonic frequency components. In many practical embodiments, the carrier wave has a frequency that is smaller than the frequency of the fundamental frequency component of the AM waveform by at least one or two orders of magnitude.

The acoustic vibration is localised in a region 5 at a given location within the object 2. The carrier wave is selected to provide the desired localization of the acoustic vibration. The degree of localization is dependent on the wavelength, and so the frequency fc of the carrier wave is chosen accordingly.

The acoustic vibration causes vibration of the object 2 in the region 5. The AM waveform is selected to provide a vibration of the object 2, which is of greater magnitude than the carrier wave at the frequency of at least one of the frequency components of the AM waveform that is utilized, preferably the fundamental frequency component. As the carrier wave is selected to provide localization of the acoustic vibration to achieve the desired resolution, depending on the nature of object 2, the mechanical response of the object 2 might not be optimal at the frequency of the carrier wave. Thus the AM waveform is used to provide vibration of the object 2 at a lower frequency than the carrier wave, at which the magnitude of the vibration of the object 2 is greater.

In general, the method may utilize any of the frequency components of the AM waveform, but advantageously the fundamental frequency component is utilized because this generally has a larger magnitude than the harmonic frequency components, if any, and produces Doppler components of larger magnitude that are most easily separated from the scattered electromagnetic wave.

To optimize the mechanical response of the object, the frequency component of the AM waveform that is utilized, for example fa in the case of utilizing the fundamental frequency component, may be selected to have a frequency that is of the same order of magnitude as the acoustic relaxation time of the region 5 of the object 2. Such an acoustic relaxation time can be measured or derived theoretically for the type of the object 2 under investigation. Similarly, the frequency component that is utilized may be selected to have a frequency may be selected to have a frequency that provides a resonant vibration of the object.

For some types of object, the AM waveform may provide a vibration of the object 2, which is, at the frequency of the frequency components of the AM waveform utilized, of a magnitude that is greater than the carrier wave by one or more orders of magnitude. In such cases, the vibration of the object 2 at the frequency of the carrier wave is by comparison insignificant and may be ignored.

As alternatives that are both illustrated in FIG. 1, the acoustic vibration may be localised in two dimensions in a region 5a (shown in dashed outline) that is limited in extent perpendicular to the propagation direction of the acoustic vibration but extends along the propagation direction, or may be localised in three dimensions in a region 5b (shown in dotted outline) that is also limited along the propagation direction. The localisation of the acoustic vibration may be achieved using conventional equipment as described in more detail below. When localised in three dimensions, along the direction of propagation of the acoustic wave, the acoustic vibration might be localised only instantaneously as the acoustic wave propagates. In many fields of application such as medical imaging, the acoustic vibration is ultrasonic.

In the simplest embodiment, the acoustic vibration is localised at a single location at a given time, that location being scanned over the object 2 so that the acoustic vibration is applied to regions 5 at a plurality of different regions 5 successively. Such scanning may be performed by using an acoustic transducer apparatus 4 which has a controllable focus or beam, or alternatively by physically moving the acoustic transducer apparatus 4 with fixed focus or beam, for example using a mechanical translator. The scanning may be carried out in one, two or three dimensions.

In more complicated embodiments, the acoustic vibration is localised in regions 5 at plural locations simultaneously but in this case the AM waveform of the acoustic vibration is different in different locations, as discussed further below.

The system 1 also includes a transmitter arrangement comprising a transmitter antenna 6 connected to a radio frequency source 7 controlled by the control unit 3 that supplies the antenna 6 with a drive signal that outputs a corresponding electromagnetic wave. Thus the transmitter arrangement in operation illuminates the object 2 with an illuminating electromagnetic wave, typically having a radio frequency, and having a sufficiently broad beam to cover the entire volume of the object 2 under investigation, ideally uniformly. The illuminating electromagnetic wave is desirably a continuous wave rather than a pulse. In this case, the illuminating electromagnetic wave has a constant amplitude and frequency, at least over the period for which the interaction with the acoustic wave is monitored by receiving the scattered Doppler components.

For ease of detection, the illuminating electromagnetic wave is predominantly of a single frequency, but in general the illuminating electromagnetic wave could include a band of frequencies. The frequency of the illuminating electromagnetic wave is greater than the frequency of the acoustic vibration, preferably by at least an order of magnitude.

The illuminating electromagnetic wave is scattered by the object 2. Within the region 5, there is an interaction between the object 2 that is vibrated by the acoustic vibration and the illuminating electromagnetic wave, which causes the acoustic vibration of the object 2 in the region 5 to modulate the scattered electromagnetic wave. In particular, the scattered electromagnetic wave that is generated includes components at the frequency of the illuminating electromagnetic wave and Doppler components at frequencies shifted from the frequency of the illuminating electromagnetic wave by frequencies of the vibration of the object and multiples thereof. This includes Doppler components at frequencies shifted from the frequency of the illuminating electromagnetic wave by frequencies of the frequency components of the AM waveform and multiples thereof. Amplitude modulation is used as described above to provide a greater magnitude of vibration at a frequency of at least one frequency component of the AM waveform than at a frequency of the carrier wave, so the Doppler components arising from the carrier wave are of lower magnitude and in many cases insignificant and may be ignored.

Figure 4A:
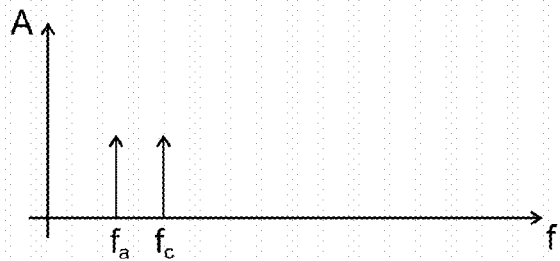
FIGS. 4a to 4c are graphs of the frequency spectrum of the acoustic vibration, the illuminating electromagnetic wave and the scattered electromagnetic wave.
Figure 4B:
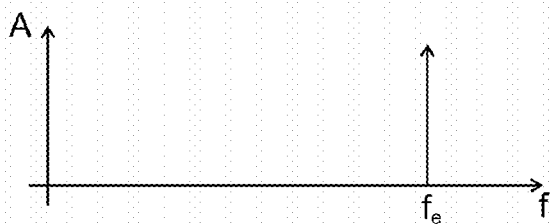
Figure 4C:
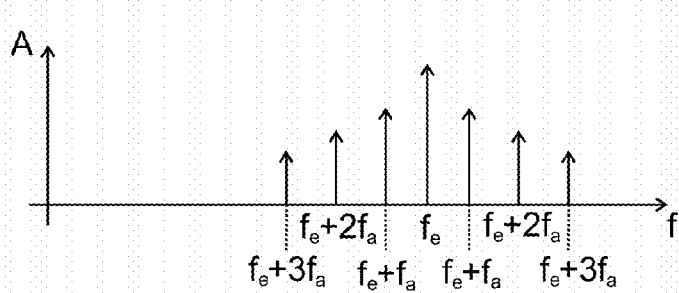

This is illustrated graphically in FIGS. 4a to 4c which are graphs of the frequency spectrum of the acoustic vibration, the illuminating electromagnetic wave and the scattered electromagnetic wave, respectively. In this example, the acoustic vibration comprises the carrier wave at a frequency fc and a fundamental frequency component of frequency fa, as shown in FIG. 2. The illuminating electromagnetic wave has a single EM frequency of fe.

The scattered electromagnetic wave comprises a central component of the EM frequency fe of the illuminating electromagnetic wave.

The scattered electromagnetic wave also comprises Doppler components (sidebands) at frequencies fe±n·fa, where n is an integer, i.e. shifted from the EM frequency fe of the illuminating electromagnetic wave by the frequency fa of the fundamental frequency component of the AM waveform and multiples thereof. Although FIG. 4c illustrates an example with three Doppler components on each side, in general there could be any number of Doppler components depending on the physical interaction. The Doppler components arising from vibration at the frequency fc of the carrier are not shown in FIG. 4c, being less significant.

Where the AM waveform also comprises harmonic frequency components, there will be further Doppler components shifted from the EM frequency fe of the illuminating electromagnetic wave by the frequency of the harmonic frequency components of the AM waveform and multiples thereof. However these further Doppler components overlap the Doppler components shown in FIG. 4c of order two or greater, and so are difficult to separate.

The physical phenomenon behind the generation of the scattered electromagnetic wave including the Doppler components is that boundaries between areas in the object 2 having different electrical properties such as conductivity and dielectric permittivity (or more generally areas where those electrical properties change) scatter the illuminating electrical magnetic wave and that vibration of those boundaries modulates the scattered wave. Thus it may be considered that the central component having the frequency of the illuminating electromagnetic wave corresponds to the scattering of the object 2 when stationary, whereas the Doppler components are generated by the vibration of the object 2.

Indeed this physical phenomenon for the general case of a vibrating object is of itself known, for example as disclosed in Lawrence et al., "Electromagnetic Scattering from Vibrating Penetrable Objects Using a General Class of Time-Varying Sheet Boundary Conditions", IEEE Transactions on Antennas and Propagation, Vol. 54, no. 7, pp. 2054-2061, July 2006. However this document merely considers the electromagnetic wave scattered by metallic and dielectric bodies which are vibrating without considering how the vibration is generated. In contrast in the present invention, the acoustic vibrations are applied localised in a region 5, meaning that the any detected Doppler components in the scattered electromagnetic wave are known to have been generated in the region 5. On this basis the system 1 uses the Doppler components to provide information about the object 2 at the location of the region 5. In particular the detected Doppler components are dependant on the mechanical response (compliance) of the object 2 at the location of the region 5 to the acoustic vibration and also on the electrical properties of the object 2 at the location of the region 5. By applying the acoustic vibration to regions 5 at different locations it is possible to build up an image of the object 2.

A detailed mathematical analysis of the interaction is given later.

The system 1 also includes a receiver arrangement comprising a receiver antenna 8 connected to signal processing apparatus 9 controlled by the control unit 3. The receiver antenna 8 is tuned to the frequency of the illuminating electromagnetic wave and is matched to the measurement medium, that is the object 2 and/or any medium (e.g. air or an acoustic matching medium) provided between object 2 and the receiver antenna 8. In operation, the receiver antenna 8 receives the scattered wave and supplies it to the signal processing apparatus 9 which analyses it to detect the Doppler components arising from the frequency component of the AM waveform that is utilized, and to output a signal representing the phase and amplitude of the Doppler components, or in general any characteristics of the Doppler components.

In FIG. 1, the acoustic transducer apparatus 4 and the transmitter antenna 6 are shown alongside each other so that the propagation direction of the acoustic vibration and the electromagnetic wave are the same, but this is not essential and other arrangements are described below. In general, the locations of the acoustic transducer apparatus 4 and the transmitter antenna 6 relative to each other are chosen so that the vibration direction of the acoustic vibration has a component parallel to the propagation direction of the illuminating electromagnetic wave. This is to generate the Doppler scattering.

The magnitude of the scattered Doppler components is maximised by the vibration direction of the acoustic vibration being parallel to the propagation direction of the illuminating electromagnetic wave. The vibration direction is parallel to the propagation direction of the acoustic vibration, so this corresponds to the acoustic vibration and the illuminating electromagnetic wave having parallel or anti-parallel directions. This is because, the mechanical movement of the region 5 resolved along the propagation direction of the illuminating electromagnetic wave is greatest in this direction, ignoring secondary motions which may be induced in other directions due to mechanical distortion of bulk material. If there is an angle $\alpha$ between the direction of the acoustic vibration and the propagation direction of the illuminating electromagnetic wave, then the velocity of the acoustic vibration resolved along the propagation direction of the illuminating electromagnetic wave is reduced, scaling with $\cos(\alpha)$. This has the effect that the magnitude of the scattered Doppler components is similarly reduced, scaling with $\cos(\alpha)$. Effectively this means that the vibration direction of the acoustic vibration should not be perpendicular to the propagation direction of the illuminating electromagnetic wave, and is preferably parallel, although the Doppler components may still be observed with higher angles $\alpha$.

The acoustic transducer apparatus 4 and the transmitter antenna 6 may be located adjacent one another to set the direction of the acoustic vibration parallel to the propagation direction of the illuminating electromagnetic wave. An exactly parallel condition is limited by the constraints imposed by the physical bulk of the acoustic transducer apparatus 4 and the transmitter antenna 6 but they may be arranged sufficiently close to be parallel for the practical purpose of maximising the Doppler scattering. Alternatively, the transmitter antenna 6 may be arranged on the opposite side of the object 2 from the acoustic transducer apparatus 4.

In general, the receiver antenna 8 may be located at any angle relative to the propagation direction of the electromagnetic wave and the vibration direction of the acoustic vibration. This is because the scattered Doppler components can in principle be scattered in any direction. The direction of scattering depends on the physical properties of the object 2 in the region 5.

Advantageously, the scattered electromagnetic wave is received along a line parallel or antiparallel to the propagation direction of the illuminating electromagnetic wave because the scattering is typically strong in these directions. Reception along a line antiparallel to the propagation direction of the illuminating electromagnetic wave may be achieved by the transmitter antenna 6 and the receiver antenna 8 being located close together (subject to the constraints imposed by their physical bulk) or being replaced by a common antenna connected to appropriate circuitry (such as a directional coupler) to isolate the frequency source 7 from circuitry handling the detected Doppler components.

However, the scattered electromagnetic wave may be received in other directions. Advantageously, the scattered electromagnetic wave is received in plural directions. This can provide additional information on the nature of object 2 in the region 5 because the direction of scattering depends on the physical properties of the object 2 which causes the scattering.

The selection of the acoustic vibration and the illuminating electromagnetic wave will now be discussed.

As the Doppler components are generated from the interaction caused by the acoustic vibration of the region 5, the resolution of the image data 13 is equal to the size of that region 5 as governed by the degree of localisation of the acoustic vibration achieved by the acoustic transducer apparatus 5. The resolution is therefore dependent on the frequency fc of the carrier wave in a similar manner to ultrasound imaging. Thus the present imaging technique can achieve similar resolution to that achieved by ultrasound imaging. For example the resolution might be less than a millimeter at very high ultrasound acoustic frequencies (roughly speaking, 1 mm resolution corresponds to a frequency of 1 MHz, 100 µm to 10 MHz, and 1 µm to 100 MHz).

The frequency of the acoustic wave controls the resolution and is therefore chosen to be sufficiently high to achieve the desired resolution having regard to the features of interest in the object 2 being imaged. The frequency of the acoustic wave may be subject to practical constraints similar to those with conventional ultrasound imaging, such as the frequencies achievable by the acoustic transducer apparatus 4, and the penetration of the acoustic waves in the object 2 being imaged.

The frequency fc of the carrier wave is selected having regard to the desired resolution and also having regard to the depth of penetration that is achievable at different frequencies. Generally, it is necessary to balance these two factors, again in a similar manner to ultrasound imaging. Typically, the frequency fc of the carrier wave may be in a range extending from 10 kHz to 1 GHz. In the case that the object is a biological object, such as human or animal tissue, typically the frequency fc of the carrier wave may be in a range extending up from 1 MHz, preferably up from 2 MHz, and/or extending up to 50 MHz, preferably up to 10 MHz. Such frequencies are ultrasonic, although in general acoustic frequencies in the audible range could in principle be used in some fields of application.

The AM waveform of the acoustic vibration is chosen having regard to the mechanical properties of the object 5 to provide vibration of desired magnitude, in the manner discussed in detail above. Typically the frequency component of the AM waveform that is utilized, generally the fundamental frequency of the AM waveform, has a frequency in a range extending from 1 Hz to 100 MHz. In the case that the object is a biological object, such as human or animal tissue, then the frequency of the frequency component that is utilized is preferably in a range extending up from 10 kHz, preferably up from 100 kHz, and/or extending up to 1 kHz.

The EM frequency of the illuminating electromagnetic wave is selected as follows. The image contrast mechanism is different from ultrasound imaging being dependent on the physical interaction between the acoustic vibration and the illuminating electromagnetic vibration and providing information on the mechanical response (compliance) of the object 2 to the acoustic vibration and on the electrical properties of the object 2, as discussed above, for example providing similar information to MRI without the requirement for magnets. Thus the present imaging technique can be seen as an alternative to other imaging modalities. The degree of absorption of the illuminating electromagnetic wave in the object 2 increases with its frequency. Thus the frequency of the illuminating electromagnetic wave is chosen to be sufficiently low to provide absorption in the object 2 which is sufficiently low to allow the entire object 2 to be imaged.

Thus, the EM frequency is chosen having regard to the electromagnetic properties of the object 2 in order to provide useful information about the object 2. In general the illuminating electromagnetic wave is a radio wave having an EM frequency in a range extending up to 30 THz, that is in the Terahertz band or below; up to 300 GHz, that is in the EHF (Extremely High Frequency) band or below, corresponding to microwave frequencies or below; or in some fields of application up to 100 GHz. In the case that the object 2 is a biological object such as human or animal tissue, advantageously the range extends up to 100 GHz, preferably up to 2 GHz. This means that the interaction in the object 2 provides information on the electromagnetic properties of the object 2 similar to MRI imaging.

The lower limit of the EM frequency is dependent on the ability of the signal processing apparatus 9 described below to separate the Doppler components from the EM frequency, noting that there is a limit in practice on how wide an EM envelope created by the amplitude modulation that can be detected, as known in the field of wideband frequency modulation. Therefore, typically the illuminating electromagnetic wave has an EM frequency in a range extending up from a value of twice said frequency component of the AM waveform, preferably ten times said frequency component of the AM waveform.

The object 2 may have a response which varies at different frequencies. Therefore, the imaging may be performed with acoustic vibrations of different frequencies and/or with an illuminating electromagnetic wave of different frequencies. The different frequencies may be applied at different times by repeating the operation of the system 1 but adjusting the acoustic frequency. Alternatively different frequencies may be applied simultaneously to the same or different regions 5. The different frequencies of excitation can also be achieved by using pseudo random pulse sequences (such as maximal length sequences) or other spread spectrum techniques. In this way, information may be obtained in respect of the different frequencies of the acoustic vibrations and/or the illuminating electromagnetic wave, so the technique is a spectroscopic technique. This allows better characterization of the nature of the object 2.

The signal processing apparatus 9 includes an amplifier 10, a frequency-modulation (FM) demodulator 11 and a digital signal processor 12.

The amplifier 10 receives and amplifies the signal received by the receiver antenna 8. Due to the low SNR, the amplifier 10 is desirably a very low noise amplifier.

The amplified signal output by the amplifier 10 is supplied to an FM demodulator 11 which is arranged to detect, from the received, scattered electromagnetic wave, a Doppler component shifted from the frequency of the illuminating electromagnetic wave by the frequency of frequency component of the AM waveform utilized, typically the fundamental frequency component. The FM demodulator 11 outputs a signal representing the phase and amplitude of the Doppler component.

Figure 5:
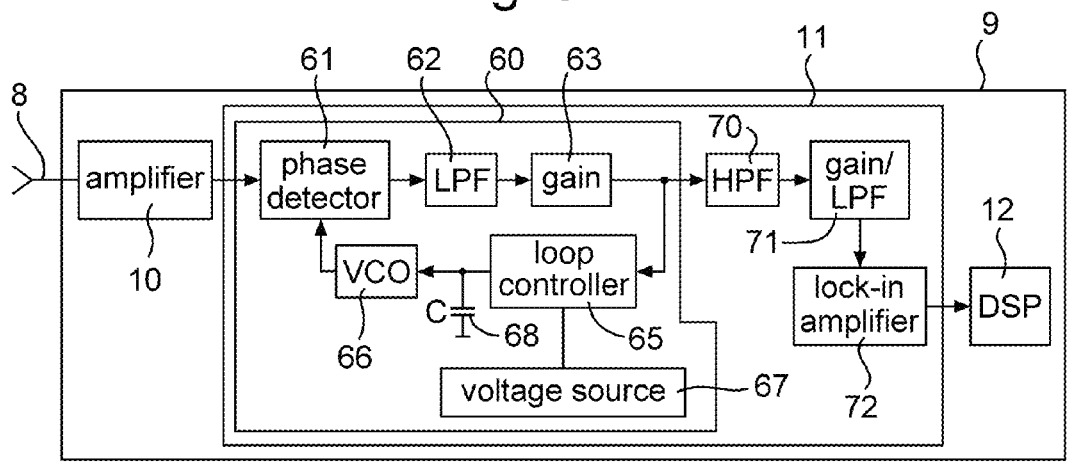
FIG. 5 is a diagram of the signal processing apparatus of the imaging system.

The FM demodulator 11 may have a detailed construction that is shown in FIG. 5 and will now be described.

The FM demodulator 11 comprises a phase-locked loop (PLL) 60 that is supplied with the scattered EM wave received by the receiver antenna 8, via the amplifier 10. The PLL 60 comprises a phase detector 61, a low pass filter 62, a gain stage 63, as well as a loop controller 65 and a voltage controlled oscillator (VCO) 66 connected in a negative feedback loop. As described below, the PLL 60 is locked to the EM frequency, and so the VCO 66 outputs a signal at that EM frequency. The phase detector 61 is supplied with the scattered electromagnetic wave and with the output of the VCO 66. The phase detector 61 outputs the phase error between its two input signals which is supplied through the low pass filter 62 and the gain stage 63 to form the output signal. The output signal therefore contains the frequency-demodulated signal comprising the set of Doppler components frequency-demodulated from the EM frequency.

This frequency-demodulated signal is also passed back as a feedback signal in the negative feedback loop to the loop controller 65. The loop controller 65 inverts the feedback signal before supplying it to the VCO 66, so has to control the VCO 66 to output a signal having the same EM frequency as the main component of the scattered electromagnetic wave. The loop controller 65 is therefore arranged as a Type I fixed gain controller, since this design is likely to provide a relatively low noise. The loop controller 65 also shifts the level of the feedback signal to adjust the centre frequency of the output of the VCO 66.

Two specific configurations for the PLL 60 are as follows.

The first configuration is intended to be used with an EM frequency of 790 MHz. In this first configuration:

the phase detector 61 is a Minicircuit ZX05-10L+, 10-1000 Mhz, 3 dBm, Lo DBD mixer;

the low pass filter 62 is a Minicircuit SLP-2.5+, 2.5 MHz cut off, low pass filter; and the VCO 60 is a Minicircuit ZX95-800C+, −97 dbc/Hz noise at 1 kHz, 790 MHz centre frequency.

These components are chosen for their low noise. For example, the phase detector 61 is a diode mixer that produces a negligible amount of noise, despite having a non-linear phase response.

In this first configuration, the loop controller 65 is a heavily decoupled AD797 operational amplifier in a negative feedback configuration. The loop gain is chosen to be minus 100 dB as a compromise between output noise and locked frequency range, since higher gain will increase the noise to less desirable doubles.

The voltage shifting is accomplished by referencing the non-inverting input of the loop controller 65 to a very low noise voltage source 67, for example provided by an analog device ADR445 that produces a voltage of 5V that may be devalued by a potential divider. This reference is decoupled using a large decoupling capacitor (not shown) to minimize any potential 1/f noise in its output level.

The output of the loop controller 65 is supplied to the VCO 66 through a low pass filter 68 that is a single pole low pass filter consisting of a RC circuit, in order to reduce distortion and increase stability.

During startup, the voltage source 67 is adjusted to vary the output voltage of the loop controller 65. In particular, the voltage level fluctuates as the loop controller 65 stabilizes. A more convenient method is to change the input voltage slightly (for example by the order of 5 mV), which has the same effect. The operating DC points sets the voltage of the VCO 66, which needs to correspond to the EM frequency of 790 MHz, within 10 kHz.

The feedback gain has been tested empirically to give acceptable knowledge performance. Another potential improvement is to provide two stages of amplifiers in the feedback loop, with the additional amplifier acting as a DC offset. This would allow the DC shift that needs to be corrected on startup, although at the cost of a small increase of noise levels.

A second configuration is intended to be used with an EM frequency of 434 MHz. In this second configuration:

the phase detector 61 is a Minicircuit ZX05-10L+, 10-1000 Mhz, 3 dBm, Lo DBD mixer;

the low pass filter 65 is a Minicircuit LPF-BOR3+, 0.3 MHz cut off low pass filter; and the VCO 60 is a Crystek CVSS-940, −110 dbc/Hz noise at 1 kHz, 434 MHz centre frequency.

The second configuration the PLL 60 remains essentially the same as the first configuration, except that for a voltage regulator used to supply the VCO 66.

In this second configuration, the components are substantive to reduce noise pickup.

The VCO 66 in this configuration is a high stability crystal based oscillator with a very low phase noise, which has been found to be a significant source of noise.

The circuit has been tested with and without the low pass filter 68 on the input to the VCO 66. It has been found that a large capacitance in the low pass filter 68 improves the SNR by a small but significant amount, whilst reducing the lock range. In this second configuration, the time constant of 0.03 s has been empirically determined to be optimal.

The output of the PLL 60 is supplied to the lock-in amplifier 72, through a high pass filter 70 and a gain stage 71 that also acts as a low pass filter, so that the high pass filter 70 and gain stage 71 together act as a band pass filter. The lock-in amplifier 72 uses a reference frequency signal that a reference frequency equal to the frequency of the utilized frequency components of the AM waveform, which is typically the fundamental frequency component of the AM waveform. Thus the reference frequency is selected to be at a frequency of vibration of the object 2 caused by the acoustic vibration. By way of comparison, if the acoustic vibration were to comprise a single frequency component (which is not in accordance with the first aspect of the invention) then the reference frequency would be the frequency of that single frequency component.

As described above, the utilized frequency component may be any of the frequency components of the AM waveform and multiples thereof, but is generally the fundamental frequency component fa of the AM waveform. The reference frequency for the PLL 60 and may be derived from a frequency source that is also used to derive the AM waveform (as described further below) and that output a signal of frequency fa. Accordingly, the acoustic transducer apparatus 4 may be connected to the FM demodulator 11 as shown in FIG. 1 to supply the AM waveform or a signal of frequency fa from the frequency source to the lock-in amplifier 72.

The lock-in amplifier 72 is arranged to extract from the frequency-demodulated signal supplied thereto a signal at the reference frequency. Thus, the lock-in amplifier 72 extracts the desired Doppler component. The lock-in amplifier 72 is further configured to generate the amplitude and phase of the extracted signal, although it could equally be configured to generate other characteristics thereof.

Figure 6:
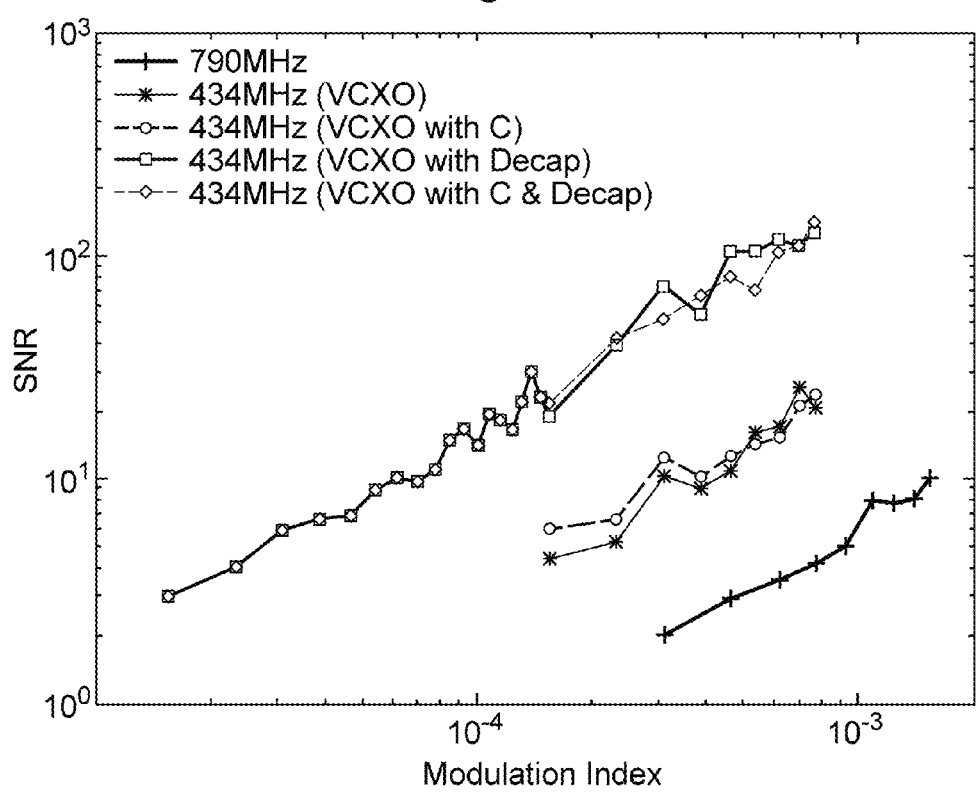
FIG. 6 is a graph of SNR against modulation index for some specific constructions of the signal processing apparatus.

This configuration of the FM demodulator 11 combining the PLL 60 and the lock-in amplifier 72 has been found to provide very sensitive detection of the Doppler component despite the relatively low signal level thereof. In frequency modulation terms, embodiments of the FM demodulator 11 have been found to be capable of detecting modulation indexes of the order of 10 parts in 1 million. This high sensitivity is achieved by the combination of the PLL 60, which effectively extracts the full set of Doppler components, and the lock-in amplifier 72 that subsequently extracts the desired one of the Doppler components, typically at the frequency fa of the fundamental frequency component. By way of example, FIG. 6 shows the performance of the first configuration (EM frequency of 790 MHz) and the second configuration (EM frequency of 434 MHz) with and without use of the capacitor in the low pass filter 68 (referred to as 'C' in FIG. 6) and with a separate decoupling capacitor (referred to as 'Decap' in FIG. 6) with a is lock-in time constant $\tau$. For example, this shows that the second configuration can achieve a sensitivity index k (SNR/MI) of around 17000.

To facilitate the FM demodulation, the FM demodulator 11 is provided with the signal of the illuminating electromagnetic wave from the frequency source 7 and with the signal of the utilized frequency component of the AM waveform of the acoustic wave from the acoustic transducer apparatus 4.

The amplifier 10 and FM demodulator 11 may be formed by analog circuits, but digital circuits could alternatively be used for any part of the amplifier 10 and FM demodulator 11. For example, a digital implementation of the lock-in amplifier 72 is particularly advantageous when plural regions 5 are simultaneously imaged as discussed below.

The signal representing the phase and amplitude of the Doppler component derived by the FM demodulator 11, in particular output by the lock-in amplifier 72, are supplied to the digital signal processor 12 which processes those characteristics of the Doppler components. As the FM demodulator 11 detects characteristics of Doppler components at frequencies shifted from the frequency of the illuminating electromagnetic wave by frequencies of the frequency components of the AM waveform and multiples thereof, those characteristics are known to have been derived from the region 5 of the object 2 at the current location of the acoustic vibration. The digital signal processor 12 is supplied with information by the control unit 3 identifying the current location of the acoustic vibration. The digital signal processor 12 stores image data 13 representing those characteristics detected in respect of each location as the location is scanned over the object 2. The image data 13 may be stored, displayed and/or output from the signal processing apparatus 9.

The digital signal processor 12 may store only the actually derived values of the phase and amplitude or other characteristics. These vary in dependence on the properties of the object 2 at different locations as discussed above and therefore provide a useful image even without further processing.

Optionally, the digital signal processor 12 may further process the actually derived values of the phase and amplitude or other characteristics, on the basis of a model of the interaction between the acoustic vibration and the illuminating electromagnetic wave, to derive characteristics representing particular physical properties of the object 2 which are also stored as image data 13. Such processing may provide information on properties of the object 2 which are more useful than the phase and amplitude themselves. For example in the case of medical imaging, such processing may be used to characterise metabolite species which have known electromagnetic responses.

The digital signal processor 12 may be implemented by a computer apparatus executing an appropriate program, optionally being the same computer apparatus as used to implement the control unit 3.

The connection from the radio frequency source 7 to the FM demodulator 11 shown in FIG. 1 may be omitted in the case that the FM demodulator 11 has the construction shown in FIG. 5. However, in an alternative construction of the FM demodulator 11 in which the PLL 60 is replaced by a coherent detector, this connection is used to supply the coherent detector with the drive signal output by the radio frequency source 7 having the EM frequency of the illuminating electromagnetic wave. In this alternative, the coherent detector uses that signal to detect signals at the EM frequency and therefore produces an output signal of a similar form to the PLL 60. The acoustic transducer apparatus 4 and various variations thereof will now be described.

As previously mentioned, the acoustic transducer apparatus 4 provides acoustic vibration is localised in a region 5 at a given time, that is localised in two dimensions in a region 5a that extends in the propagation direction or localised in three dimensions in a region 5b that is limited in the propagation direction. This may be achieved using a conventional apparatus that may provide a controllable focus or a fixed focus.

Figure 7:
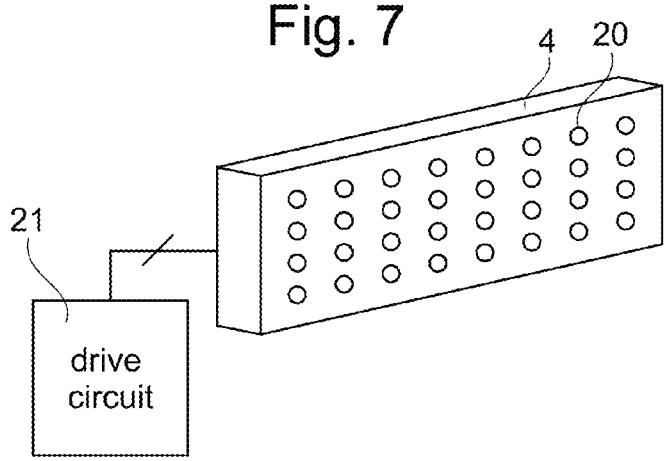
FIG. 7 is a perspective view of an acoustic transducer apparatus of the imaging system.

FIG. 7 shows a possible arrangement in which the acoustic transducer apparatus 4 comprises an array of transducers 20 which provide an electronically controllable focus at a region 5. In this case, the acoustic wave output by the array of transducers 20 may be a propagating beam. As known in the field of ultrasound imaging such beam-forming allows a high energy focus is formed at a desired location. In the present method this means that the majority of the scattered electromagnetic wave contains information pertaining to the region 5 of focus.

To provide localisation in two dimensions, the array of transducers 20 may apply the acoustic vibration as a continuous beam, so that the acoustic vibration is localised in space within the propagating beam in the two dimensions perpendicular to the direction of propagation. To provide localisation in three dimensions, the array of transducers 20 may still apply the acoustic vibration as a beam that is not continuous so that along the third dimension in the direction of propagation, the acoustic vibration is localised instantaneously as the acoustic wave propagates. The propagating beam may be a pulse which is localised in a single region 5 at a given time which region 5 propagates through the object 2 over time. Alternatively the propagating beam may have an AM waveform of varying frequency so that different frequencies are localised in different regions 5 simultaneously. Accordingly, the information supplied by the control unit 3 to the digital signal processor 12 indicates the timing of the propagating beam, thereby identifying the current location of the acoustic vibration.

In the case that the propagating beam has an AM waveform of varying frequency, one option is that the signal processing apparatus 9 is arranged to perform a Fourier Transform, or other transform, of the received scattered signal into the time domain. Due to the different frequencies of acoustic vibration being localised in different regions 5 simultaneously, such a transform generates the characteristics in respect of each of the different regions 5. In this way, a "movie" can be constructed and images as a function of time can be displayed with extremely high temporal/spatial resolution.

To form the propagating beam, the acoustic transducer apparatus 4 comprises a drive circuit 21 which provides a separate drive signal to each transducer 20 which drive signals vary in amplitude and/or phase and/or delay to form the focus at the desired region 5. Such formation of a beam from an array of transducers is known in itself, for example in the field of ultrasound imaging.

Figure 8:
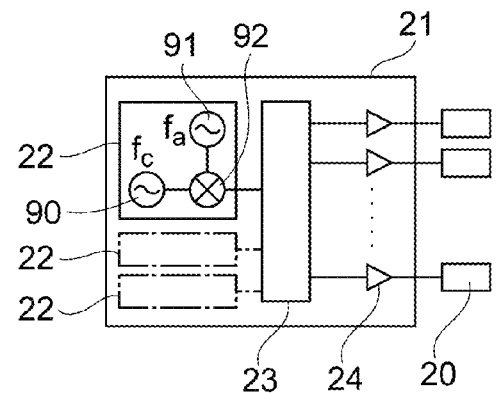
FIG. 8 is diagram of a drive circuit of the acoustic transducer apparatus.

As shown in FIG. 8, the drive circuit 21 includes a waveform generator 22 which generates an oscillating signal having a waveform corresponding to the desired waveform of the and supplies it to a beamformer circuit 23. The beamformer circuit 23 may be implemented in analog or digital means. The waveform generator 22 comprises a carrier frequency source 90 that outputs a signal having the frequency fc of the carrier wave, and an AM waveform source 91 that outputs the AM waveform, which in the simplest case may comprise a fundamental frequency component of frequency fa. The waveform generator 22 also comprises a mixer 92 that mixes the two signals output by the carrier frequency source 90 and the AM waveform source 91 to derive the oscillating signal.

The beamformer circuit 23 derives a signal for each transducer 20 from the oscillating signal by modifying the amplitude and/or phase and/or delay by respective amounts that shape the overall acoustic vibration output from the acoustic transducer apparatus 4 into a beam. The beamformer circuit 23 operates under the control of the control unit 3 to provide a focus in a desired region 5. The drive circuit 21 also includes amplifiers 24 for amplifying the signal for each transducer 20 output by the beamformer circuit 23 to form the drive signal which is then supplied to the respective transducers 20.

Figure 9:
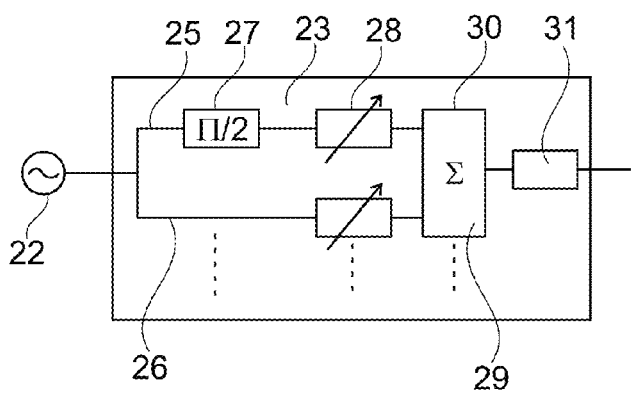
FIG. 9 is a diagram of a beamformer circuit of the drive circuit.

The beamformer circuit 23 may include programmable amplifiers (or attenuators) and/or phase shifters and/or delays to modify the oscillating signal. For example, the beamformer circuit 23 may employ a quadrature arrangement as shown in FIG. 9 in respect of each one of the transducers. This quadrature arrangement comprises an I-channel 25 and a Q-channel 26 each supplied with the oscillating signal from the waveform generator 22. The I-channel includes $\pi/2$ phase delay 27 for phase-delaying the oscillating the oscillating signal so that the signals in the I-channel 25 and Q-channel 26 are in quadrature. The I-channel 25 and Q-channel 26 each include respective attenuators 27 and 28, the outputs of which are supplied to an adder 30 for adding the attenuated quadrature signals. The respective degrees of attenuation provided by each of the attenuators 27 and 28 may be controlled to thereby vary the amplitude and phase of the signal output by the adder 30.

This signal output by the adder 30 is optionally provided to a variable delay circuit 31 which may be varied to control the delay of the drive signal.

The drive circuit 21 may be formed by analog circuits, but digital circuits could alternatively be used for any part thereof.

Figure 10:
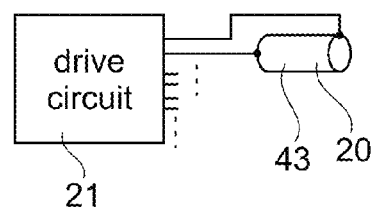
FIG. 10 is a perspective view of a transducer of the acoustic transducer apparatus.

Each transducer 20 may be formed as shown in FIG. 10 by a piece 43 of piezoelectric material (or other electroactive material). The drive signal from the drive circuit 21 is applied across the piece 43 of piezoelectric material which vibrates in response thereto thereby generating an acoustic wave. The piece 43 of piezoelectric material is shown as being cylindrical but may be shaped to direct the generated acoustic wave.

In FIG. 7, the array of transducers 20 is illustrated as a 2D planar array, but in general any arbitrary form of array may alternatively be used, for example a 1D linear or conformal array, a curved or conformal 2D array, a 3D array, or plural arrays on different sides of the object 2.

As an alternative to forming a beam, this acoustic transducer apparatus 4 comprising the array of transducers 20 may apply the acoustic vibration as a spot which is continuously localised in space in three dimensions.

Using this acoustic transducer apparatus 4 comprising an array of transducers 20, the location of the region 5 at which the acoustic vibration is localised may be scanned over the object 2 under electronic control to derive information on different regions 5 and thereby build up an image of the object 2.

In the case that the acoustic vibration is localised in two dimensions, then the image is a two dimensional image (or shadow image) whose pixels contain information from the entirety of the region 5a that extend through the object 2 along the propagation direction of the acoustic vibration. In this case, a three dimensional image can be built up by moving the acoustic transducer apparatus 4 and transmitter antenna 6 around the object 2 under examination and taking a series of images with different angles of incidence. Then the series of images may be transformed into a three dimensional image using similar transforms to those conventional for other types of imaging such as computed tomography (CT) scanning.

In the case that the acoustic vibration is localised in three dimensions, then a three-dimensional image may be derived by scanning the region 5b in three dimensions.

Such scanning could also be achieved using an acoustic transducer apparatus 4 which has a fixed focus, by physically moving the acoustic transducer apparatus 4.

As previously mentioned, in the simplest embodiment, the acoustic vibration is localised in a single region 5 at a given time, the acoustic vibration being applied to regions 5 at a plurality of different locations successively.

In more complicated embodiments, the acoustic vibration is localised in plural regions 5 at different locations simultaneously. In this case, the acoustic vibration has an AM waveform including utilized frequency components, normally the fundamental frequency components, having different frequencies in different regions 5.

One option is to use the acoustic transducer apparatus 4 comprising an array of transducers 20 as described above but modified to simultaneously produce plural propagating beams with AM waveforms of different frequencies. This may be achieved by replicating the circuitry of the drive circuit 21, as described above and shown in FIG. 8, in respect of each of the different frequencies used. The drive signals in respect of each frequency may be summed and applied to the respective transducers 20. Whilst it would be possible to replicate the entire circuitry of the drive circuit 21 described above, more conveniently, merely the waveform generator 22 is replicated, as shown in dotted outline in FIG. 8. The same or different carrier frequencies fc may be used to provide localisation in each region 5 but in the case of using the same carrier frequencies fc then a common carrier frequency source 90. In the case that the waveform generator 22 is replicated, the beamformer circuit 23 performs two functions. Firstly, in respect of each waveform generator 22, the beamformer circuit 23 derives a signal for each transducer 20 from the oscillating signal by modifying the amplitude and/or phase and/or delay suitable for producing a beam directed to the respective region. Secondly, the beamformer circuit 23 sums the derived signals in respect of each transducer 20 to derive a summed signal that is supplied to the respective amplifiers 24. As the acoustic vibration has different frequencies in different regions 5, the scattered electromagnetic wave has Doppler components of different frequencies generated in the different regions 5, each having frequencies shifted from the frequency of the illuminating electromagnetic wave by the different frequencies of the frequency component of the AM waveform of the acoustic vibration (and multiples thereof). The signal processing apparatus 9 is therefore arranged to detect and derive characteristics of the different Doppler components which are known to have been generated at the different locations of the regions 5. This may be achieved by the signal processing apparatus 9 being arranged as described above but within the FM demodulator 11 replicating the lock-in-amplifier 72 in respect of each of the acoustic frequencies used. This is discussed in further detail below.

In this manner, characteristics of the Doppler components and therefore image data 13 may be simultaneously be derived in respect of plural regions 5. Many regions 5 may be simultaneously imaged in this manner. This approach is limited by the ability of the signal processing apparatus 9 to discriminate between Doppler components of different frequencies.

In some arrangements, plural regions 5 are simultaneously imaged allowing an image to be derived without scanning the regions 5. In other arrangements, plural regions 5 are simultaneously imaged but then the regions 5 are scanned to image other areas of the object 2. For example, one particular embodiment may employ a plurality of propagating beams arranged in a 1D (or 2D) array to simultaneously image a 1D (or 2D) slice which propagates through the object 2 allowing successive slices to be imaged, thereby building up a 2D (or 3D) image in a similar manner to conventional medical ultrasound imaging as employed for example in obstetric sonography. Thus, the use of plural regions 5 allows an image to be scanned more quickly than if a single region 5 is used, thereby improving the image acquisition period. This is a particular advantage in the case of imaging a living object as it reduces the length of time for which the object needs to be stationary.

Alternatively, the system 1 may be implemented to investigate the properties of the object 2 in a single region 5 without providing imaging across the object 2. In this case, acoustic vibration is applied to just a single region 5. This may be achieved with the system 1 as described above but modifying the control implemented by the control unit 3. Alternatively, the system 1 may be simplified, for example using an acoustic transducer apparatus 4 having a fixed focus because scanning is not required.

When investigating the properties of the object 2 in a single region 5, it is particularly advantageous to use acoustic vibrations of different frequencies and/or with an illuminating electromagnetic wave of different frequencies, as described above. The different frequencies may be applied at different times but or simultaneously. In the latter case it is possible to tune the system 1 to simultaneously investigate a wide range of frequencies without needing to use the different frequencies to obtain information on regions 5 at different locations as is necessary with some imaging implementations.

The size and detailed construction of the system 1 will depend on the field of application. For example for use in medical imaging, the system 1 might be realised as a dedicated device in which the acoustic transducer apparatus 4 is similar to an ultrasound head in a conventional ultrasound imaging apparatus. In this case, the transmitter antenna 6 and receiver antenna 8 might be integrated into the same ultrasound head.

Optionally, the system 1 might additionally incorporate an acoustic system 14 connected to the acoustic transducer apparatus and arranged to receive a reflected acoustic wave from each of the regions 5 and thereby to derive acoustic image data 15 with derivation of the image data 13 by the signal processing apparatus 9. The acoustic system 14 may be arranged as conventional ultrasound imaging apparatus, thereby allowing the present method to be integrated with conventional ultrasound imaging. The acoustic image data 15 and the image data 13 may be registered with each other in space and time, for example using conventional image registration techniques, allowing the system 1 to simultaneously produce two different types of image. This is advantageous in many fields, for example as a real time system for dynamic diagnostics and monitoring.

Similarly the system 1 might be integrated with an ultrasound treatment system, allowing monitoring of state of the object 2 during treatment.

Some examples of the system 1 applied to different applications in the field of medical imaging wherein the object 2 is human tissue are shown in FIGS. 7 to 9. In each case, the transmitter antenna 6 and receiver antenna 8 are replaced by a common antenna 16 connected to the radio frequency source 7 and the signal processing apparatus 9 via a directional coupler 17 that provides separation of the transmitted and received signals.

Figure 11:
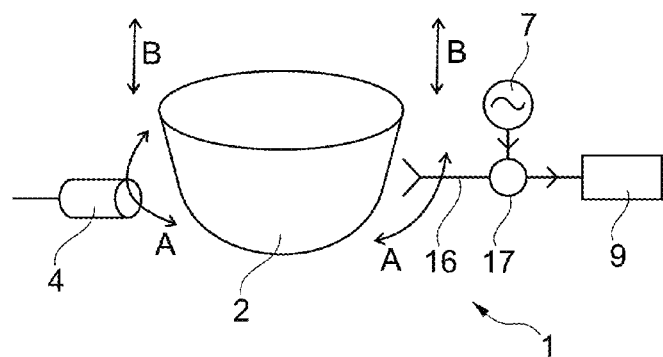
FIG. 11 is a perspective view of the imaging system applied to mammography.

FIG. 11 illustrates the system 1 applied to mammography in which the object 2 is a breast. The acoustic transducer apparatus 4 and common antenna 16 are arranged on opposite sides of the breast, preferably with a matching medium between the breast and the acoustic transducer apparatus 4, for example oil, matching gel or a flexible membrane. The acoustic transducer apparatus 4 produces a narrow beam of acoustic vibration localised in two or three dimensions. The acoustic transducer apparatus 4 and common antenna 16 are rotated together as shown by the arrows A to obtain information from different directions that may be combined to derive a two dimensional image slice. Plural such image slices may be obtained by moving the acoustic transducer apparatus 4 and common antenna 16 up and down as shown by the arrows B.

Figure 12:
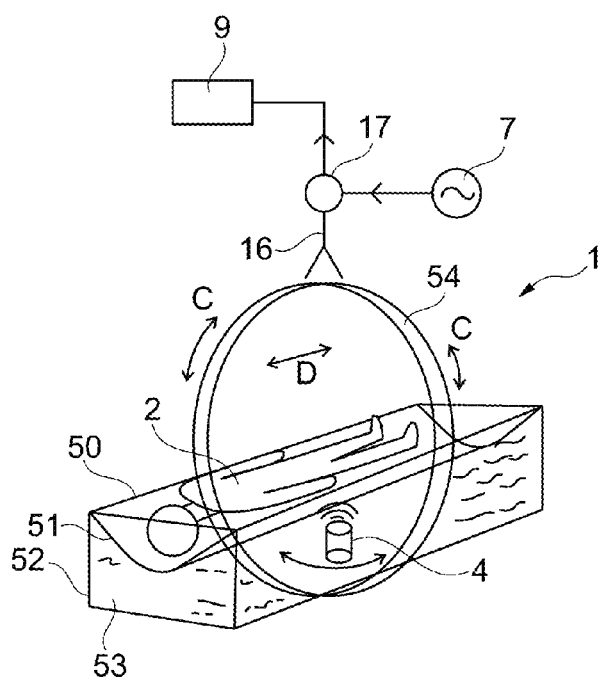
FIG. 12 is a perspective view of the imaging system applied as a full body scanner.

FIG. 12 illustrates the system 1 applied as a full-body scanner in which the object 2 is the body of a human subject. The system 1 includes a bed 50 that comprises a flexible membrane 51 supported across the top of a bath 52 of containing matching medium 53. The subject lies on the flexible membrane 51 below the level of the matching medium 53. The acoustic transducer apparatus 4 and common antenna 16 are supported opposite one another on a rotatable gantry 54 that extends around the bath 52 so that the acoustic transducer apparatus 4 and common antenna 16 are on opposite sides of the subject. Rotation of the gantry 54 as shown by the arrows C allows information to be obtained from different directions that may be combined to derive a two dimensional image slice. Plural such image slices may be obtained by moving the gantry 54 as shown by the arrows B.

Figure 13:
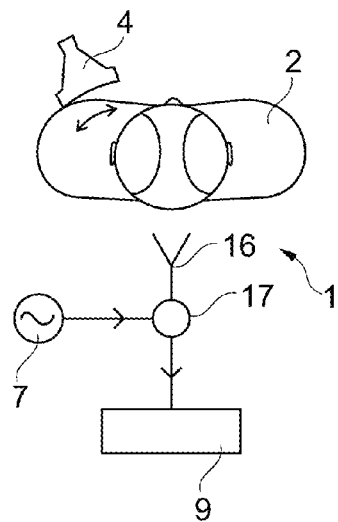
FIG. 13 is a perspective view of the imaging system applied using a hand-held acoustic transducer apparatus.

FIG. 13 illustrates the system 1 applied implementing the acoustic transducer apparatus 4 as a conventional hand-held apparatus of the type used for scanning a subject, for example during pregnancy. In this case, the common antenna 16 is simply arranged beneath the subject, for example beneath a bed on which the subject lies, and the acoustic transducer apparatus 4 is used in a conventional manner to simultaneously obtain an image in accordance with the present invention and a conventional acoustic image.

A detailed mathematical analysis of the interaction giving rise to the scattered electromagnetic wave is now given. This explanation is given in terms of the Acoustic Radiation Force (ARF) generated by the acoustic vibration.

ARF has been extensively studied from its theoretical discovery by Rayleigh and Langevin. In summary, ARF is generated by acoustic wave propagation though a boundary of differing acoustic impedances in the direction of the wave vector. ARF is usually associated with focused ultrasound, and have been used clinically for Acoustic Radiation Force Imaging (ARFI) for measuring tissue stiffness.

ARF is generated from a sum of two pressures: Rayleigh radiation pressure, defined as the difference between the average pressure with and without movements caused by the acoustic wave, and Langevin radiation pressure from the difference between the mean pressure caused by absorption or reflection of the impedance boundary. In this application, since we are looking at the movement of boundary between tissues, the Langevin radiation pressure is the main focus.

The Langevin ARF can be calculated from a plain wave using:

$$F = \frac{2\alpha I}{c}$$

where I is the peak temporal average intensity, $\alpha$ is the attenuation coefficient of the boundary between tissues, and c is the velocity of the acoustic wave. In the case of the present acoustic vibration, I is the peak temporal average intensity of the carrier wave. Due to the amplitude modulation, this average intensity and hence the force vary with the AM waveform. The force causes movements in the object 2 generated by the frequency components of the AM waveform, in the same way as ARFI, which causes frequency modulation to any illuminating electromagnetic radiation. By appropriate selection of frequency of the AM waveform, the vibration of the object 2 caused thereby can be of significantly greater magnitude than the magnitude of the vibration at the frequency of the carrier wave. From numerical simulation and other published results, for the case of an object that is a biological sample, the peak displacement is expected to be of the order of 10 μm.

When an infinite sheet of dielectric boundary vibrate in an electromagnetic plane wave $U_0 e^{i\omega t}$, the back scatter field at the boundary can be approximated by assuming quasi-static moving boundary condition and non-relativistic effect:

$$U = \rho U_0 e^{i[\omega t + 2kA \sin(\omega_a t)]}$$

where $$k = \frac{\omega_0}{c}$$

or the wave number of the electromagnetic wave, and A is the boundary's amplitude of vibration. The back scattered wave experience periodic phase modulation with maximum shift of ±2 kA radians. The maximum deviation is rewritten as:

$$\beta = 2kA$$

where $\beta$ is called the modulation index. It is proportional to the vibration amplitude, which is in turn proportional to the stiffness of the target boundary. In the proposed system, ARF is used to excite a small region of a dielectric boundary, leading to Doppler shift. The acoustic vibration may be spatially scanned to obtain a raster scan of the target. Such a raster scanning method also allows automatic registration of the ultrasound pulse echo imaging as well as the EMA data, and this is used in the two dimensional measurements of lambs' kidneys described below.

Since the area is small compared to the wavelength of the EM wave, full diffraction calculations is needed to see the effect of the interaction between excited and unexcited areas, so that both of these phase contributions are considered. The diffraction effects are derived initially for any circular symmetric functions, then specifically for a uniformly excited circular region within a circular dielectric disc, and finally in case of a Gaussian distributed excitation.

Figure 14:
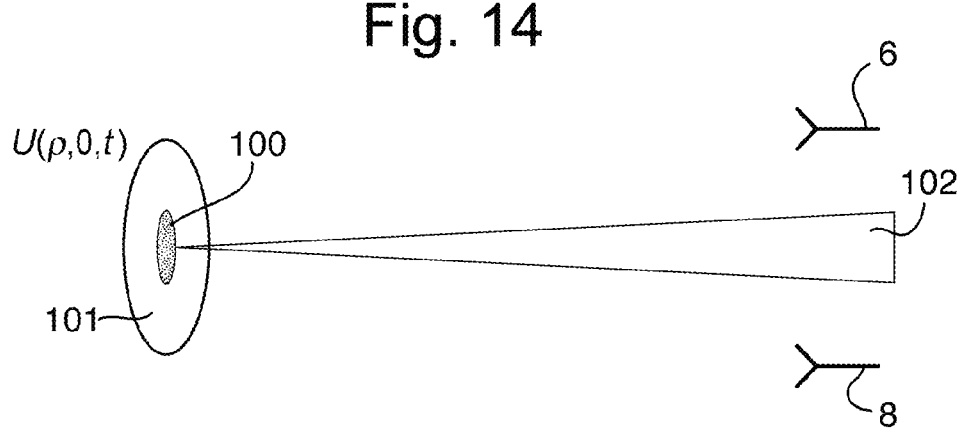
FIG. 14 is a schematic diagram of an ARF excited area caused by a focused acoustic vibration.
Figure 15:
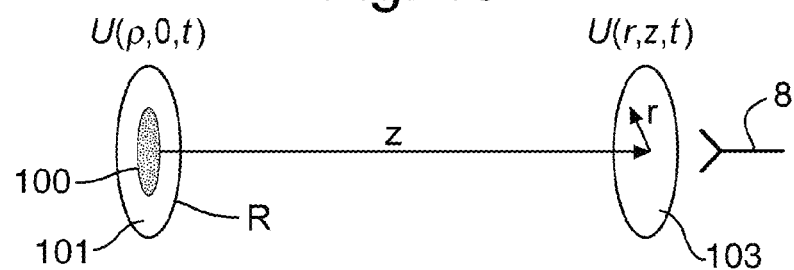
FIG. 15 is a schematic diagram of diffraction planes showing a source field and a farfield.

Reference is made to FIG. 14 which is a schematic diagram of an ARF excited area 100 at the dielectric boundary caused by a focused acoustic wave 102, and FIG. 15 which is a schematic diagram of diffraction planes showing the source electric field formed by the ARF excited area 100 on the left, and the far-field on the right. Consider a cylindrical coordinate system for two planes, one being a 'source' plane 101 where the excited area 100 is placed and the other being an 'observer' plane 103 where the receiver antenna 8 is located, where U(ρ,0,t) is the circular symmetric electric field distribution at the 'source' plane 101, and U(r,z,t) is the diffracted field at the 'observer' plane 103, z meters away. Under the far field condition, it is possible to use Fraunhofer approximation to the diffraction equation, provided that the far-field condition $$z > \frac{2D^2}{\lambda}$$

is met, D is the characteristic size of the scattering region, i.e. the maximum extent of the dielectric, and $\lambda$ is the wavelength of the electromagnetic wave. Using this approximation, the circular symmetric diffraction equation becomes [6]:

$$U(r, z, t) = A \cdot \int_0^\infty \rho U(\rho, 0, t) J_0\left(\frac{kr\rho}{z}\right) d\rho \quad (4)$$

where $$A = \frac{k\Gamma e^{j\frac{2\pi z}{\lambda}} e^{j\frac{\pi r^2}{\lambda z}}}{jz},$$

$\Gamma$ is the reflection coefficient associated with the dielectric disc, and $J_0$ is the zeroth order Bessel function of the first kind. The reflection coefficient $\Gamma$ can be determined from the dielectric contrast by solving Maxwell's equation at the dielectric boundary:

$$\Gamma = \frac{\eta_2 - \eta_1}{\eta_2 + \eta_1} \quad (5)$$

where $\eta = \sqrt{\mu/\epsilon}$ or the refractive index of the material. It was also noted that changes in conductivity could also cause reflection, which could be used for imaging inclusions with high salinity. Apply a sinusoidal vibration to the disc, we can separate the electric field at the 'source' plane 101 to spatial and temporal components:

$$U(r, z, t) = A \cdot \int_0^\infty \rho U_0(\rho, 0) e^{j\omega t + j\beta\phi(\rho)\cos(\arctan(\frac{r}{z}))\cos(\omega_a t)} J_0\left(\frac{kr\rho}{z}\right) d\rho \quad (6)$$

The spatially dependent $$\beta\phi(\rho)\cos\left(\arctan\left(\frac{r}{z}\right)\right)\cos(\omega_a t)$$

phase term comes from the sinusoidal Doppler shift due to varying spatial amount of excitation, $\beta$ is the modulation index. Since only the phase shift is needed in the received signal, the expression can be rewritten as a sum of the real and imaginary parts and factoring out the constant angular velocity $e^{j\omega t}$:

$$\text{Real: } A \cdot \int_0^\infty \rho U(\rho, 0) J_0\left(\frac{kr\rho}{z}\right) \cos\left(\beta\phi(\rho)\cos\left(\arctan\left(\frac{\rho}{z}\right)\right)\cos(\omega_a t)\right) d\rho \quad (7)$$

Imaginary:

$$A \cdot \int_0^\infty \rho U(\rho, 0) J_0\left(\frac{kr\rho}{z}\right) \sin\left(\beta\phi(\rho)\cos\left(\arctan\left(\frac{\rho}{z}\right)\right)\cos(\omega_a t)\right) d\rho$$

If $\beta \ll 1$ (which will be the case for displacements of $10^{-6}$ m), they are simplified to:

$$\text{Real: } A \cdot \int_0^\infty \rho U(\rho, 0) J_0\left(\frac{kr\rho}{z}\right) d\rho \quad (8)$$

Imaginary: $A \cdot \cos\left(\arctan\left(\frac{\rho}{z}\right)\right)$ $$\cos(\omega_a t) \cdot \int_0^\infty \rho U(\rho, 0) J_0\left(\frac{kr\rho}{z}\right) \beta\phi(\rho) d\rho$$

The phase can be calculated by taking the arctan of the ratio of the two components. This is approximated by ignoring the higher order terms to give the phase modulation in the far field:

$$\text{Phase} = \frac{\int_0^\infty \rho U(\rho, 0) J_0\left(\frac{kr\rho}{z}\right) \phi(\rho) d\rho}{\int_0^\infty \rho U(\rho, 0) J_0\left(\frac{kr\rho}{z}\right) d\rho} \beta\cos\left(\arctan\left(\frac{\rho}{z}\right)\right)\cos(\omega_a t) \quad (9)$$

So the effective modulation index $\beta$ is multiplied by the ratio of the spatial Fourier transform of the excited area divided by the spatial Fourier transform of the unexcited area.

A simple example is to use uniform circular excitation area that lies within a dielectric disc shown in FIG. 15. Assuming that the source plane 101 has been illuminated with plane electromagnetic wave, the resulting phase modulation becomes:

$$\text{Phase} = \frac{r_0 J_1\left(\frac{kr_0 r}{z}\right)}{R J_1\left(\frac{kRr}{z}\right)} \beta\cos\left(\arctan\left(\frac{\rho}{z}\right)\right)\cos(\omega_0 t) \quad (10)$$

where the on-axis modulation is simply the ratio of the two areas:

$$\text{Phase} = \frac{r_0^2}{R^2} \beta\cos\left(\arctan\left(\frac{\rho}{z}\right)\right)\cos(\omega_a t) \quad (11)$$

Figure 16:
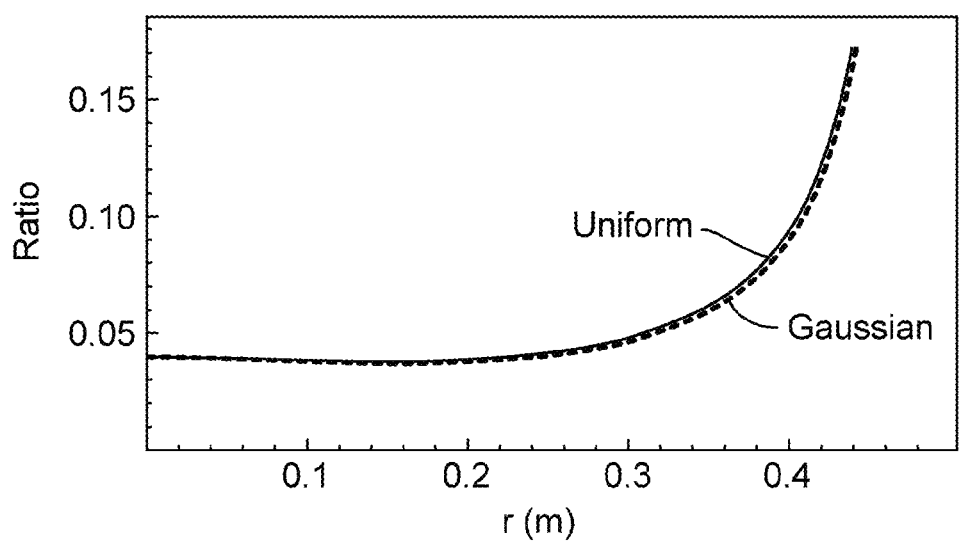
FIG. 16 is a graph of the reduction factor in a modulation index against position for a Gaussian excitation.

With typical values expected to be used, the ratio is plotted against the displacement in the 'observer' plane 103 in FIG. 16 which is a plot of the reduction factor in the modulation index using z=0.2 m; wavelength=0.04 m; r0=0.002 m; R=0.01 m; $r_0^2/r_1^2$=0.04.

The ratio increases to reach 1 when the receiver is placed at the null of the far-field pattern caused by the dielectric disc, where $\beta$ is maximum. This is where the receiving antenna should be placed.

A Gaussian acoustic excitation is also calculated, since this will likely represent the excitation in practice. The waist of the excitation is set to be the same as the radius in the uniform excitation $r_0$:

$$\text{Phase} = \frac{\int_0^\infty \rho U(\rho, 0) J_0\left(\frac{kr\rho}{z}\right) e^{\left(\frac{-r^2}{r_0^2}\right)} d\rho}{\int_0^\infty \rho U(\rho, 0) J_0\left(\frac{kr\rho}{z}\right) d\rho} \beta\cos\left(\arctan\left(\frac{\rho}{z}\right)\right)\cos(\omega_a t) \quad (12)$$

FIG. 16 also shows the result for Gaussian excitation. It provides slightly slower increase in beta as the receiver moves away from the axis, while the maximum is located at the same location compared to the uniform excitation. We observe that the overall effect of the unmodulated region is to lower the modulation index at the receiver, scaling linearly with the ratio of the area of excited to unexcited region. Therefore, the current EMA system uses a narrow horn antennas to minimise returns from unexcited region.

Figure 17:
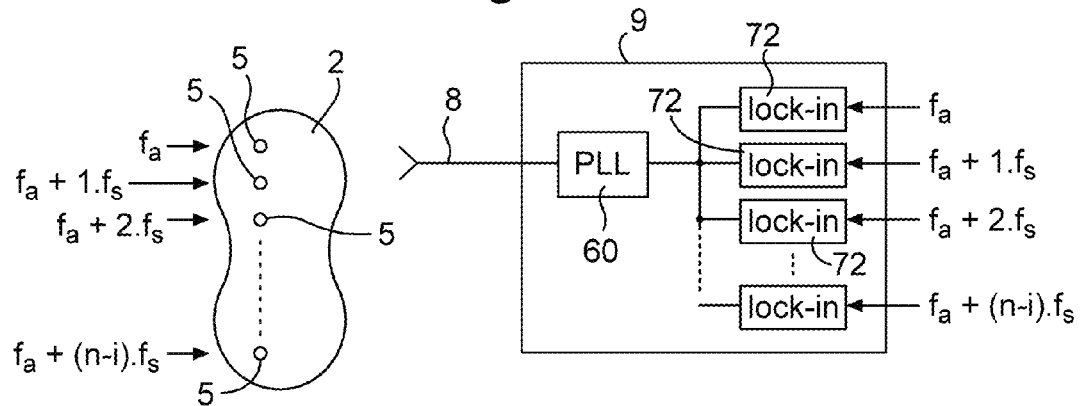
FIG. 17 is schematic diagram of the imaging system in a multi-channel configuration.

There is now discussed further the application of acoustic vibration with different frequencies in different regions 5 in order to provide simultaneous scanning of the different regions. In particular, in each of the different regions 5, the AM waveform of the acoustic vibration may be selected to be different by having different fundamental frequency components, for example of frequencies fa, (fa+fs), (fa+2·fs), . . . , (fa+(n−1)·fs), where fs is the frequency separation between the fundamental frequency components and n is the number of different frequencies used. Each different acoustic vibration is localized in a different region 5 of the object 2, as illustrated schematically in FIG. 17.

The signal processing apparatus 9 is arranged to detect and derive characteristics of Doppler components from each of the different acoustic vibrations, typically the Doppler component generated by the different fundamental frequency components. This may be achieved by the signal processing apparatus 9 being arranged as described above but, within the FM demodulator 11, the lock-in-amplifier 72 being replicated in parallel in respect of each of the acoustic frequencies used, for example as illustrated schematically in FIG. 17. As each different Doppler component is known to have been generated at a different region 5, this provides parallel scanning of the object over n frequency channels of separation fs.

The selection of the different frequency channels will now be discussed.

The frequency channels are selected having regard to the SNR as follows.

The modulation index is a linear function of the amplitude of the vibration, which is in turn proportional to the probe power output. The SNR is finally calculated using:

$$SNR = k \cdot \tau \cdot \alpha \cdot I$$

where k is the sensitivity index, $\tau$ is the lock-in time constant of the lock-in amplifier 72, $\alpha$ is a proportionality constant and I is the power density from the acoustic transducer apparatus 4. Alternatively the power density is proportional to the power output P:

$$I = \frac{P}{A}$$

where A is the ARF excited area.

In a low SNR regime, the time constant limits the scan time of a single data point, since an extended integration time is needed for an acceptable imaging SNR and the power density of the ARF is fixed for safety reasons. For N scanning pixels, the scanning time T decreases directly with the number of channels n available:

$$T = \frac{N\tau}{n}$$

In practice, the number of channels available is a function of the minimum frequency separation fs. This is determined by the filter bandwidth of the lock-in amplifiers 72, so that the frequency channels do not overlap. This bandwidth is inversely proportional to the time constant $\tau$. The total bandwidth available is determined by the frequency response of the tissue, which is typically in the range of 100 Hz. For tissue bandwidth B, the maximum number of channels $n_B$ can be expressed using:

$$n_B = B\tau$$

For N scanning pixels, the minimum time needed to complete a scan ($T_{min}$) is given by:

$$T_{min} = \frac{N\tau}{n_B} = \frac{N}{B}$$

Combining these equations, the minimum number of channels required to obtain a desired minimum scan time is therefore:

$$n_{min} = \frac{B \cdot SNR}{k\alpha I}$$

The number of channels cannot in general increase indefinitely, since the power available to the acoustic transducer apparatus 4 is limited. The maximum number of channels $n_{max}$ is simply the maximum power output available divided by the required power output:

$$n_{max} = \frac{P_{max}}{P}$$

Figure 18:
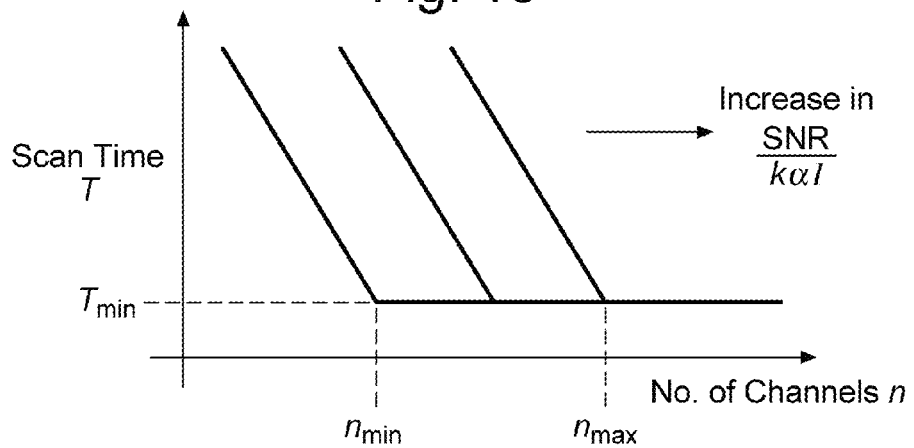
FIG. 18 is a graph of scan time against the number of channels using such a multi-channel configuration.

FIG. 18 is a graph of the scan time against the number of channels n illustrating these two regimes.

In the imaging system described above in the second configuration with a decoupling capacitor, the SNR is estimated to be 5 for time constant of 1 s and ultrasound intensity of 0.9 W/cm$^2$, giving a as $3.3\times10^{-4}$ cm$^2$/Ws. The tissue bandwidth is typically of the order 100 Hz. For an image of 40×40 pixels and using is time constant to achieve the desirable SNR, this equates to 100 channels to reach the minimum total scan time of 16 seconds. The SNR can be increased by increasing number of channels and time constant, but the total scan time remains constant.

To decrease the scan time further, it is necessary to use a higher modulation frequency, which can be accomplished by using demodulator with higher sensitivity index.

The simplest method of parallel scanning uses an acoustic transfer apparatus 4 comprising multiple single focus transducers, for example NDT (non-destructive testing) transducers, to produce spatially fixed ARF excitation areas for mechanical scanning. The number of transducers is the same of the number of channels required. However, they can be of the same type and frequency, which could simplify the manufacturing process. Their physical separation of the transducers allows effective heat dissipation and higher acoustic intensity, which translates to higher imaging SNR.

Since it is difficult to integrate large number of focusing transducers, the maximum number of channels is limited. The use of 10 channels is conceivable, and using the current receiver parameters, the scanning time is simply divided by the number of channels, for example as follows:

Scan time for 1 channel 40×40 pixels: 1600×1 s/60=26 minutes (SNR of 5)

Scan time for 10 channel 40×40 pixels: 1600×1 s/60/10=2 6 minutes (SNR of 5)

Scan time for 10 channel 40×40 pixels: 1600×0.5 s/60/10=1.3 minutes (SNR of 2.5)

In most clinical ultrasound machines, the transducer consists of individually programmable delay piezo elements in a 1D linear phased array. The output power of these systems is lower than a typical NDT transducer, which requires longer lock-in time for the same SNR. For example, the lock-in time typically required may be roughly 10 times longer for a single channel measurement. The advantage of a 1D linear phased array is the ability to form arbitrary intensity distribution in the sample on the fly, so it is possible to use back propagating algorithms to generated areas that are modulated at different frequencies. Due to the 1D nature of the probe, it is difficult to control the wavefront to generate large number of ARF regions uniformly for different channels. It is estimated that the maximum number of channels achievable is close to 20, therefore producing the following scan times:

Scan time for 1 channel linear array 40×40 pixels: 1600× 10 s/60=260 minutes (SNR of 5)

Scan time for 10 channel linear array 40×40 pixels: 1600×10 s/60/20=13 minutes (SNR of 5)

Scan time for 10 channel linear array 40×40 pixels: 1600×5 s/60/20=7.5 minutes (SNR of 2.5)

Extending the 1D concept, there maybe used a 2D phased array of transducers operating similarly to 1D array. The generation of a scattered wave is more robust due to the large number of elements available, using holographic waveform generation as known in the art. This would allow implementation of a large number of channels, for example of the order of 100. Allowing for the same power density in the 1D probe, the scan times are as follows:

Scan time for 1 channel 2D array 40×40 pixels: 1600×10 s/60=260 minutes (SNR of 5)

Scan time for 100 channel 2D array 40×40 pixels: 1600× 10 s/60/100=2.6 minutes (SNR of 5)

Scan time for 100 channel 2D array 40×40 pixels: 1600×5 s/60/100=1.3 minutes (SNR of 2.5)

There will now be described two experimental examples of the method of the present invention.

Figure 19:
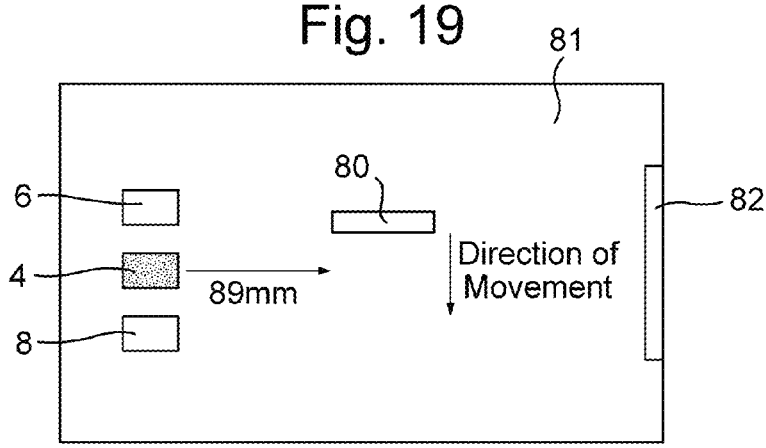
FIG. 19 is a schematic view from above of the imaging system configured to perform a first experimental example.

The first experimental example was performed using the imaging system 1 of FIG. 1 arranged in a configuration shown in FIG. 19. The object 2 under investigation was an agar target 80 that was simply a block of agar. The agar target 80 was arranged in a tank 81 of water to allow good coupling and power transfer from the acoustic transducer apparatus 4 which was a focused non-destructive testing ultrasonic transducer with the following parameters:

| Make | Olympus |
|---|---|
| Diameter | 1.25 inch |
| Focal length | 3.5 inch |
| Centre frequency | 2.25 MHz |
| Focal spot size | 3.8 mm |
| Acoustic power density (average) | 100 mW/mm$^2$ |

The transmitter antenna 6 and the receiver transmitter 8 were immersed in the tank 81 of water in a bistatic configuration alongside the acoustic transducer apparatus 4. The illuminating electromagnetic wave had an EM frequency of 800 MHz. The path attenuation at this frequency is well within acceptable limits for the radar signal link budget. The acoustic transducer apparatus 4 was arranged to provide a beam of acoustic vibration localised in two dimensions. The agar target 80 was moved perpendicular to the propagation direction of the acoustic vibration by a computer-controlled linear translation stage across the path of the beam at a distance of 89 mm from the acoustic transducer apparatus 4 to localise the beam in successive regions across a 1D slice of the agar target 80.

A sheet 82 of neoprene was provided in the tank 81 of water in the path of the acoustic vibration behind the agar target 80 to absorb acoustic vibration, reducing reflections thereof and therefore reducing noise.

The agar target 80 was formulated to simulate the conductivity of soft tissue by the addition of a small amount of NaCl (for example at a concentration of the order of 3 g/L).

Figure 20:
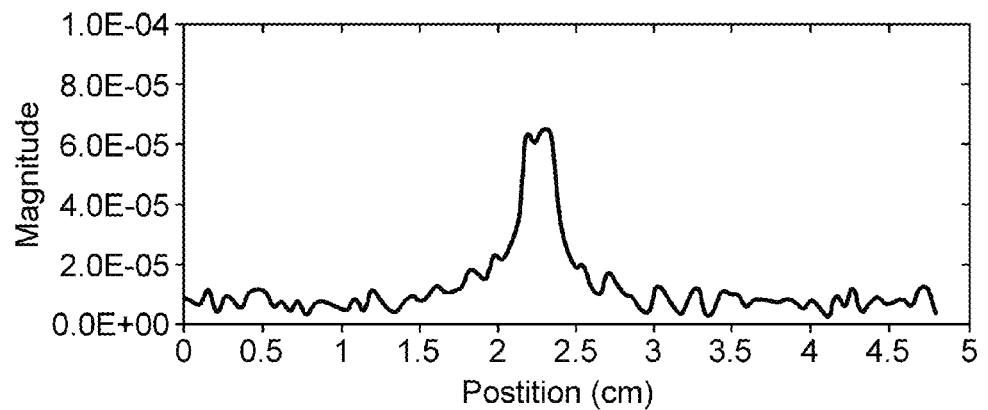
FIG. 20 is a graph of the magnitude of a Doppler component against position for a 1D slice image in the first experimental example.

The results for a particular agar target 80 are shown in FIG. 20, which is a graph of the magnitude of the detected Doppler component against the position of the agar target 80 for the case of an agar target 80 having a Young's modulus of 2.1 kPa and a diameter of 1.35 cm. This graph shows a peak as the agar target 80 crosses the beam of the acoustic vibration, and therefore is effectively a 1D slice image of the agar target 80.

To illustrate the discrimination of different conductive properties of the object 2, the experiment was repeated varying the agar target 80 to change the concentration of agar to water to vary the stiffness from 2.1 kPa to 8.5 kPa, this representing a range of stiffness that mimics healthy soft tissues.

Figure 21:
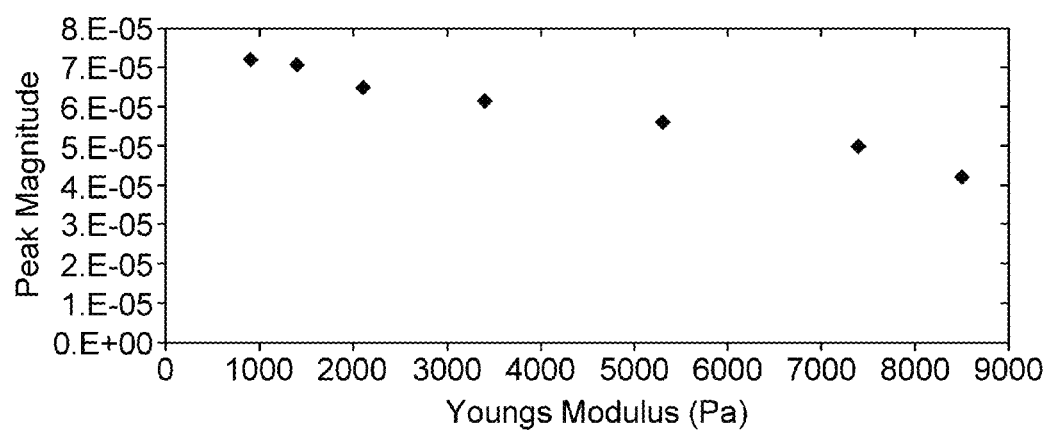
FIG. 21 is a graph of the peak magnitude of the Doppler component for agar targets of different stiffness in the first experimental example.

The results are shown in FIG. 21, which is a graph of the peak magnitude of the Doppler components in the 1D slice image plotted against the Young's modulus of the agar target 80. This graft experimentally demonstrates an approximately linear relationship as predicted by equation (3) above.

In the second experimental example, the imaging system 1 was used in the same configuration as shown in FIG. 19, but the object 2 was a lamb's kidney, instead of the agar target 80, to demonstrate scanning capability in mammalian soft tissue. The acoustic transducer apparatus 4 was again arranged to provide a beam of acoustic vibration localised in two dimensions, but the lamb's kidney was scanned in 2D, rather than in 1D, by a computer-controlled XY table in a plane perpendicular to the propagation direction of the acoustic vibration. This allowed the derivation of a 2D image from a raster scan in a plane approximately in the middle of the object. This configuration is commonly called a "C-scan" in medical vocabulary.

In a first measurement, a small incision was made into the side of the kidney and there was inserted therein a 5 mm nodule of calcium carbonate having a relative dielectric constant of 6.5, in order to simulate a kidney stone.

Figure 22:
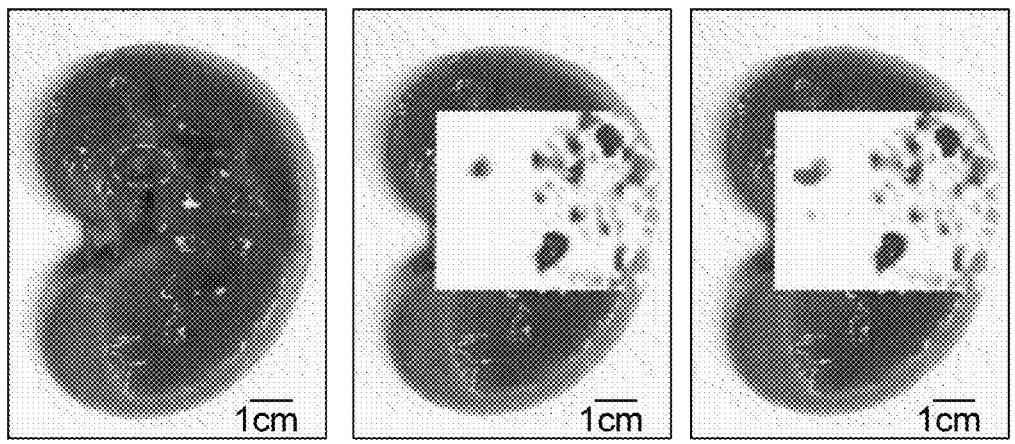
FIGS. 22 and 23 are both sets of 2D images of a lamb's kidney in a second experimental example.

At the same time as acquiring the acousto-electromagnetic image in accordance with the present method, there was acquired an ultrasonic pulse echo image. FIG. 22 shows the images acquired by both modalities superimposed on each other, the scanning area of the present method within the kidney being shown as a white overlay containing 100×80 pixels corresponding to a spatial dimension of 50×40 mm. In FIG. 22, the left image is a photograph of a post-scan dissection of the lamb's kidney showing the inserted calcium carbonate module. The middle image is the same photograph with the pulse echo image overlaid in registration. This shows the internal structure of the kidney such as the renal pyramids and the renal veins, but these occlude the kidney stone, which is not distinguishable in this mode. The right image is the photograph with the acousto-electromagnetic image in accordance with the present invention overlaid in registration. In contrast with the pulse echo image taken at the same time, the sensitivity to changes in the dielectric interface (i.e. due to the electromagnetic impedance mismatch) makes the kidney stone visible.

Figure 23:
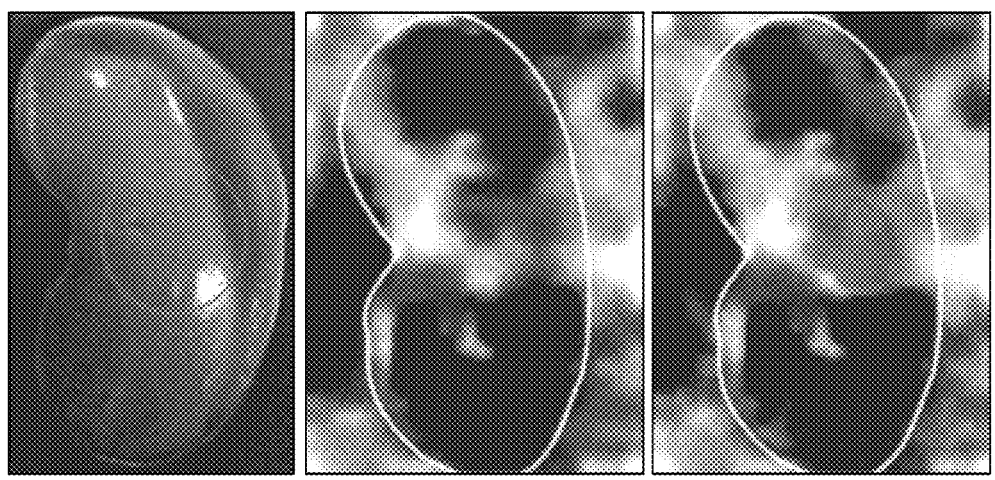

As predicted in equation (5) above, the signal acquired by the present method is dependent on the reflection coefficient caused by the dielectric band mismatch and therefore it is possible also to detect and image conductive inclusions. To test this capability, a further lamb's kidney was injected with a saturated saline solution (30 g NaCl/100 g water) in the centre to create an area of high conductivity. The further lamb's kidney was then scanned over a larger area of 100×80 mm to image the whole kidney. The images acquired using the present method are shown in FIG. 23 wherein, the left image is a photograph of the kidney with the site of the saline solution circled, the middle image is an ultrasound pulse echo image and the right image is the acousto-electromagnetic image of the injected site overlaid on the ultrasound pulse echo image. It can be seen that the site of the saline solution is not distinguishable in the ultrasound echo image, but is distinguishable in the acousto-electromagnetic image.

These results validate the suggestion from the theoretical analysis that the present method may be used to image inclusions with different dielectric conductivity properties. A simulation of a calcite kidney stone shows that the present method can be used to differentiate different tissue from the surrounding renal structure. The subsequent image of saline solution shows that changes in conductivity are also picked up.

The theoretical calculation above also suggests that modulation index, which determines the required sensitivity, can be reduced by stray reflection from regions that are not excited by ARF radar clutter and receives/transmit antenna coupling in order to combat these effects, it is desirable to prove the sensitivity of the reception of the electro scattered electromagnetic wave by using improving the sensitivity of the receiver antenna 8 and to reduce the mutual coupling and cross torque.

The invention claimed is:

1. A method of investigating physical properties of an object, comprising:
    applying to the object acoustic vibration localised in two or three dimensions in a region in the object, the acoustic vibration comprising a carrier wave that is amplitude modulated by an AM waveform, the carrier wave being selected to provide the localization of the acoustic vibration and the AM waveform including a frequency component selected to provide a vibration of the object of greater magnitude than the carrier wave;
    simultaneously illuminating the object with an illuminating electromagnetic wave that has an EM frequency in a range extending up to 30 THz, the vibration direction of the acoustic vibration having a component parallel to the propagation direction of the illuminating electromagnetic wave so that the acoustic vibration of the object in the region generates a scattered electromagnetic wave including a set of Doppler components shifted from the frequency of the illuminating electromagnetic wave by frequencies of the vibration of the object caused by the acoustic vibration and multiples thereof; and
    receiving the scattered electromagnetic wave generated in the region,
    detecting, from the received, scattered electromagnetic wave, a Doppler component shifted from the frequency of the illuminating electromagnetic wave by the frequency of said frequency component of the AM waveform; and
    outputting a signal representing at least one characteristic of the detected Doppler component.

2. The method according to claim 1, wherein said AM waveform has a fundamental frequency component, said frequency component of the AM waveform being the fundamental frequency component.

3. The method according to claim 2, wherein said AM waveform further includes other frequency components.

4. The method according to claim 3, wherein the AM waveform is a square wave.

5. The method according to claim 1, wherein said frequency component of the AM waveform has a period of the same order of magnitude as the acoustic relaxation time of the region of the object.

6. The method according to claim 1, wherein said frequency component of the AM waveform is selected to provide a resonant vibration of the object.

7. The method according to claim 1, wherein the carrier wave has a frequency in the range from 10 kHz to 1 GHz.

8. The method according to claim 1, wherein said frequency component of the AM waveform is in the range from 1 Hz to 100 MHz.

9. The method according to claim 8, wherein said frequency component of the AM waveform is in a range extending up from 10 kHz and/or extending up to 1 kHz.

10. The method according to claim 8, wherein the illuminating electromagnetic wave has a frequency in a range extending up to 2 GHz.

11. The method according to claim 1, wherein the illuminating electromagnetic wave has an EM frequency in a range extending up from a value of twice said frequency component of the AM waveform, preferably up from a value of ten times said frequency component of the AM waveform.

12. The method according to claim 1, wherein said object is a biological object.

13. The method according to claim 12, wherein said biological object is human or animal tissue.

14. The method according to claim 12, wherein the carrier wave has a frequency in a range extending up from 1 MHz and/or extending up to 50 MHz.

15. The method according to claim 1, wherein the step of detecting Doppler components comprises:
    supplying the received, scattered electromagnetic wave to a phase-locked loop locked to the EM frequency to produce a frequency-demodulated signal comprising the set of the Doppler components frequency-demodulated from EM frequency; and
    supplying the frequency-demodulated signal to a lock-in amplifier configured to extract a signal at a reference frequency equal to the frequency of said frequency component of the AM waveform.

16. The method according to claim 15, wherein the lock-in amplifier being configured to generate the amplitude and/or phase of the extracted signal, being said at least one characteristic of the detected Doppler component.

17. The method according to claim 1, further comprising:
    applying, simultaneously with said first mentioned acoustic vibration, a second acoustic vibration localised in two or three dimensions in a further region in the object, the second acoustic vibration comprising a carrier wave that is amplitude modulated by a second AM waveform, the carrier wave being selected to provide the localization of the further acoustic vibration and the second AM waveform including a frequency component of a different frequency from the first mentioned waveform of the first acoustic vibration, selected to provide a vibration of the object of greater magnitude than the carrier wave;
    detecting, from the received, scattered electromagnetic wave, a second Doppler component shifted from the frequency of the illuminating electromagnetic wave by the frequency of said frequency component of the second AM waveform; and
    outputting a signal representing at least one characteristic of the detected second Doppler component.

18. The method according to claim 1 being a method of imaging an object, wherein:
    the step of applying acoustic vibration comprises applying the acoustic vibration localised in a plurality of regions either sequentially or simultaneously but with AM waveforms including frequency components of different frequencies in each region;
    the step of receiving the scattered electromagnetic wave comprises receiving the scattered electromagnetic wave generated in each of the plurality of regions;

the step of detecting a Doppler component comprises detecting a Doppler component in respect of each region;

the step of outputting a signal comprises outputting a signal representing at least one characteristic of the detected Doppler component in respect of each region; and the method further comprises storing data representing the at least one characteristic of the detected Doppler component in respect of each region as image data.

19. A system for investigating physical properties of an object, the system comprising:

an acoustic transducer apparatus arranged to apply to the object acoustic vibration localised in two or three dimensions in a region in the object, the acoustic vibration comprising a carrier wave that is amplitude modulated by an AM waveform;

a transmitter arrangement arranged to illuminate the object with an illuminating electromagnetic wave having a frequency in a range extending down from 30 THz simultaneously with the application of acoustic vibration, the vibration direction of the acoustic vibration having a component parallel to the propagation direction of the illuminating electromagnetic wave so that so that the vibration of the object caused by the acoustic vibration in the region generates a scattered electromagnetic wave including a set of Doppler components shifted from the frequency of the illuminating electromagnetic wave by frequencies of the vibration of the object caused by the acoustic vibration and multiples thereof; and a receiver arrangement arranged to receive the scattered electromagnetic wave generated in the region; and a signal processing apparatus arranged to detect, from the received, scattered electromagnetic wave, a Doppler component shifted from the frequency of the illuminating electromagnetic wave by the frequency of a frequency component of the AM waveform, and to output a signal representing at least one characteristic of the detected Doppler component.

20. The system according to claim 19, wherein said AM waveform has a fundamental frequency component, said frequency component of the AM waveform being the fundamental frequency component.

21. The system according to claim 20, wherein said AM waveform further includes other frequency components.

22. The system according to claim 21, wherein the AM waveform is a square wave.

23. The system according to claim 19, wherein said frequency component of the AM waveform has a period of the same order of magnitude as the acoustic relaxation time of the region of the object.

24. The system according to claim 19, wherein said frequency component of the AM waveform is selected to provide a resonant vibration of the object.

25. The system according to claim 19, wherein the carrier wave has a frequency in the range from 10 kHz to 1 GHz.

26. The system according to claim 19, wherein said frequency component of the AM waveform is in the range from 1 Hz to 100 MHz.

27. The system according to claim 19, wherein the illuminating electromagnetic wave has an EM frequency in a range extending up from a value of twice said frequency component of the AM waveform, preferably ten times said frequency component of the AM waveform.

28. The system according to claim 19, wherein said object is a biological object.

29. The system according to claim 28, wherein said biological object is human or animal tissue.

30. The system according to claim 28, wherein the carrier wave has a frequency in a range extending up from 1 MHz and/or extending up to 50 MHz.

31. The system according to claim 28, wherein said frequency component of the AM waveform is in a range extending up from 10 kHz and/or extending up to 1 kHz.

32. The system according to claim 28, wherein the illuminating electromagnetic wave has a frequency in a range extending up to 2 GHz.

33. The system according to claim 19, wherein the signal processing apparatus comprises:

a phase locked-loop supplied with the received, scattered electromagnetic wave, the phase-locked loop being locked to the EM frequency and arranged to produce a frequency-demodulated signal comprising the set of the Doppler components frequency-demodulated from EM frequency; and a lock-in amplifier supplied with the frequency-demodulated signal and configured to extract a signal at a reference frequency equal to the frequency of said frequency component of the AM waveform.

34. The system according to claim 33, wherein the lock-in amplifier is configured to generate the amplitude and/or phase of the extracted signal, being said at least one characteristic of the detected Doppler component.

35. The system according to claim 19, wherein:

the acoustic transducer apparatus is arranged to apply, simultaneously with said first mentioned acoustic vibration, a second acoustic vibration localised in two or three dimensions in a further region in the object, the second acoustic vibration comprising a carrier wave that is amplitude modulated by a second AM waveform;

the signal processing apparatus is also arranged to detect, from the received, scattered electromagnetic wave, a second Doppler component shifted from the frequency of the illuminating electromagnetic wave by the frequency of said frequency component of the second AM waveform, and to output a second signal representing at least one characteristic of the detected second Doppler component.

36. The system according to claim 19, being an imaging system, wherein:

the acoustic transducer apparatus is arranged to apply the acoustic vibration localised in a plurality of regions either sequentially or simultaneously but with AM waveforms including frequency components of different frequencies in each region;

the receiver apparatus is arranged to receive the scattered electromagnetic wave generated in each of the plurality of regions;

the signal processing apparatus is arranged to detect a Doppler component a Doppler component in respect of each region, to output a signal representing at least one characteristic of the detected Doppler component in respect of each region, and to store data representing the at least one characteristic of the detected Doppler component in respect of each region as image data.

* * * * *